United States Patent [19]
Hustad et al.

[11] Patent Number: 5,976,849
[45] Date of Patent: Nov. 2, 1999

[54] HUMAN E3 UBIQUITIN PROTEIN LIGASE

[75] Inventors: Carolyn Marziasz Hustad, Wilmington, Del.; Namit Ghildyal, Kennett Square, Pa.

[73] Assignee: Zeneca Limited, London, United Kingdom

[21] Appl. No.: 09/070,060

[22] Filed: Apr. 30, 1998

Related U.S. Application Data

[60] Provisional application No. 60/073,839, Feb. 5, 1998.

[51] Int. Cl.$^6$ .............................. C12N 9/00; C12N 15/52; C12N 15/11; C07H 21/04
[52] U.S. Cl. ...................... 435/183; 435/243; 435/254.2; 435/320.1; 435/325; 435/410; 435/455; 536/23.1; 536/23.2; 536/24.3; 536/24.31; 536/24.33
[58] Field of Search ............................. 435/6, 69.1, 455, 435/440, 325, 410, 243, 254.2, 320.1, 183; 536/23.1, 23.2, 23.5, 24.3, 24.31, 24.33

[56] References Cited

PUBLICATIONS

Hochstrasser, Mark; Ubiquitin–Dependent Protein Degragation, *Annu. Rev. Genet.* 1996, 30:405–39.
Weissman, Alan M.; Regulating Degradation by Ubiquitination, *Review Immunology Today*, vol. 18, No. 4 189, Apr. 1997.
Pahl, Heike L. et al.; Control of Gene Expression by Proteolysis, *Current Opinion in Cell Biology* 1996, 8:340–347.
Rolfe, Mark et al.; The Ubiquitin–Mediated Proteolytic Pathway as a Therapeutic Area, *J. Mol. Med.* (1997) 75:5–17.
Perry, William L. et al.; The Itchy Locus Encodes a Novel Ubiquitin Protein Ligase That is Disrupted in a $^{18h}$ Mice, *Nature Genetics*, vol. 18, Feb. 1998.
D'Andrea, Alan D., Relieving the *Itch, Nature Genetics*, vol. 18, Feb. 1998.

*Primary Examiner*—John L. LeGuyader
*Assistant Examiner*—Mark L. Shibuya
*Attorney, Agent, or Firm*—Patrick H. Higgins, Esq.

[57] ABSTRACT

A novel human E3 ubiquitin protein ligase is provided as well as a nucleic acid structural region which encodes the polypeptide and the amino acid residue sequence of the human biomolecule. Methods are provided to identify compounds that modulate the biological activity of the molecule and hence regulate cellular and tissue physiology.

7 Claims, 15 Drawing Sheets

FIG.1

```
GTCGCCGCCGCCCCGAAGTCCCGGTAACCATGACATTTNACGGTGGCCTTGTGGNAGACAAC
GCCTTAACCCAAGGAAGTGACTCAAACTGTGAGAACTTCAGGTTTTCCAACCTATTGGTGGT
ATGTCTGACAGTGGATCACAACTTGGTTCAATGGGTAGCCTCACCATGAAATCACAGCTTCA
GATCACTGTCATCTCAGCAAAACTTAAGGAAAATAAGAAGAATTGGTTTGGACCAAGTCCTT
ACGTAGAGGTCACAGTAGATGGACAGTCAAGAAGACAGAAAATGCAACAACACAAACAGT
CCCAAGTGGAAGCAACCCCTTACAGTTATCGTTACCCCTGTGAGTAAATTACATTTTCGTGT
GTGGAGTCACCAGACACTGAAATCTGATGTTTTGTTGGGAACTGCTGCATTAGATATTTATG
AAACATTAAAGTCAAACAATATGAAACTTGAAGAAGTAGTTGTGACTTTGCAGCTTGGAGGT
GACAAAGAGCCAACAGAGACAATAGGAGACTTGTCAATTTGTCTTGATGGGCTACAGTTAGA
GTCTGAAGTTGTTACCAATGGTGAAACTACATGTTCAGAAAGTGCTTCTCAGAATGATGATG
GCTCCAGATCCAAGGATGAAACAAGAGTGAGCACAAATGGATCAGATGACCCTGAAGATGCA
GGAGCTGGTGAAAATAGGAGAGTCAGTGGGAATAATTCTCCATCACTCTCAAATGGTGGTTT
TAAACCTTCTAGACCTCCAAGACCTTCACGACCACCACCACCCACCCCACGTAGACCAGCAT
CTGTCAATGGTTCACCATCTGCCACTTCTGAAAGTGATGGGTCTAGTACAGGCTCTCTGCCG
CCGACAAATACAAATACAAATACATCTGAAGGAGCAACATCTGGATTAATAATTCCTCTTAC
TATATCTGGAGGCTCAGGCCCTAGGCCATTAAATCCTGTAACTCAAGCTCCCTTGCCACCTG
GTTGGGAGCAGAGAGTGGACCAGCACGGGCGAGTTTACTATGTAGATCATGTTGAGAAAAGA
ACAACATGGGATAGACCAGAACCTCTACCTCCTGGCTGGGAACGGCGGGTTGACAACATGGG
ACGTATTTATTATGTTGACCATTTCACAAGAACAACAACGTGGCAGAGGCCAACACTGGAAT
CCGTCCGGAACTATGAACAATGGCAGCTACAGCGTAGTCAGCTTCAAGGAGCAATGCAGCAG
TTTAACCAGAGATTCATTTATGGGAATCAAGATTTATTTGCTACATCACAAAGTAAAGAATT
TGATCCTCTTGGTCSATTGCCACCTGGATGGGAGAAGAGAACAGACAGCAATGGCAGAGTAT
ATTTCGTCAACCACAACACACGAATTACACAATGGGAAGACCCCAGAAGTCAAGGTCAATTA
AATGAAAAGCCCTTACCTGAAGGTTGGGAAATGAGATTCACAGTGGATGGAATTCCATATTT
TGTGGACCACAATAGAAGAACTACCACCTATATAGATCCCCGCACAGGAAAATCTGCCCTAG
ACAATGGACCTCAGATAGCCTATGTTCGGGACTTCAAAGCAAAGGTTCAGTATTTCCGGTTC
TGGTGTCAGCAACTGGCCATGCCACAGCACATAAAGATTACAGTGACAAGAAAACATTGTT
TGAGGATTCCTTTCAACAGATAATGAGCTTCAGTCCCCAAGATCTGCGAAGACGTTTGTGGG
TGATTTTTCCAGGAGAAGAAGGTTTAGATTATGGAGGTGTAGCAAGAGAATGGTTCTTTCTT
TTGTCACATGAAGTGTTGAACCCAATGTATTGCCTGTTTGAATATGCAGGGAAGGATAACTA
CTGCTTGCAGATAAACCCCGCTTCTTACATCAATCCAGATCACCTGAAATATTTTCGTTTTA
TTGGCAGATTTATTGCCATGGCTCTGTTCCATGGGAAATTCATAGACACGGGTTTTCTTTA
CCATTCTATAAGCGTATCTTGAACAAACCAGTTGGACTCAAGGATTTAGAATCTATTGATCC
AGAATTTTACAATTCTCTCATCTGGGTTAAGGAAAACAATATTGAGGAATGTGATTTGGAAA
TGTACTTCTCCGTTGACAAAGAAATTCTAGGTGAAATTAAGAGTCATGATCTGAAACCTAAT
GGTGGCAATATTCTTGTAACAGAAGAAATAAAGAGGAATACATCAGAATGGTAGCTGAGTG
GAGGTTGTCTCGAGGTGTTGAAGAACAGACACAAGCTTTCTTTGAAGGCTTTAATGAAATTC
TTCCCCAGCAATATTTGCAATACTTTGATGCAAAGGAATTAGAGGTCCTTTTATGTGGAATG
CAAGAGATTGATTTGAATGACTGGCAAAGACATGCCATCTACCGTCATTATGCAAGGACCAG
CAAACAAATCATGTGGTTTTGGCAGTTTGTTAAAGAAATTGATAATGAAGAGAATGAGAC
TTCTGCAGTTTGTTACTGGAACCTGCCGATTGCCAGTAGGAGGATTTGCTGATCTCATGGGG
AGCAATGGACCACAGAAATTCTGCATTGAAAAGTTGGGAAAGAAATTGGCTACCCAGAAG
TCATACCTGTTTTAATCGCCTGGACCTGCCACCATACAAGAGCTATGAGCAACTGAAGGAAA
AGCTGTTGTTTGCCATAGAAGAAACAGAAGGATTTGGACAAGAGTAACTTCTGAGAACTTGC
ACCATGAATGGGCAAGAACTTATTTGCAATGTTTGTCCTTCTCTGCCTGTTGCACATCTTGT
AAAATTGGACAATGGCTCTTTAGAGAGTTATCTGAGTGTAAGTAAATTAATGTTCTCATTTA
GATTTATCTCCCAGTGATTTCTACTCAGCGTTTCCAGAAATCAGGTCTGCAAATGACTAGTC
AGAACCTTGCTTAACATGAGATTTTAACACAACAATGAAATTTGCCTTGTCTTATTCCACTA
GTTTATTCCTTTAACAACAATATTTTATRTGTRTCAAAAGTCTCACTTGGGAGTAGTGTTTT
TTTCTTTTAGACATTCTGCAGACATGCAGGGAAGTCCTTTGGTAACTGCAATATACAAGATT
```

```
TTCCTATTAAGCCTCTTGGTAAGAGGCATTTGTTAAAAGTGCAAGCTTACTCCTGCTTCTGG
GGATGTGAGCAAAATTCGGGCTTGTGTTCTCCCTCTCATTTTAGTCTGACTTGACTATTGTT
TTTCCTTTCTGGCGCATGAATCCATACATCATTCCTGGAAGTGAGGCAAGACTCTTGCATCT
CTACAAAGTAGTTTTGTCAATTTGAATTCAGGGAAAAGTTGGTCACAGCCTGCAAATGACTT
CATTTGGAAGTCTGATTGTTTCAGTTGCCTGACAAATACTACACTTTACAAACAATGTTAAC
ACTGTGATTCCTTCATTGTTTTAAGAAGTTAACCTAGGGCCGGGCATGGTGGCTCATACCTG
TAATCCTAGCACTCTGGGAGGCCGAGGCAGGAGGATCCCTTTAGCCCAGGAGTTAAAGACCA
GCCTGGGCAACATAGGGAGACCCTGTCTTTTTTTGGGCAGCGTGGTGGGGATAAATAAAW
AAAARRAAAAAAAACKTAGCCTAGAATTAGAATTAATTTAATTGAATTCATCTAAAGATGTC
TCTGGTGATTTTTATATGTTCCGCTATATAATTGATGCTTTATAGTTTTATCATAATCCAAC
AACTTCAGTTATATTTAATTATTGTTAAGGAGTTTAAGACTAGAAAGACTAGAGTGCTTTCT
AGTCCAAATAGAGGTCAGTGAAACAGCTTTTGACATCAGATTTTCATTTGAGAGGGAGAGCT
GTGGTACTGGCTAAAAGAAAGGAAGATAACATCCAGTAACCACAGGAATATATTCTCTGTG
AATTAAAAGTCTTCAAAGTTATCATTTCTCTGACATATGTTGGAGTAGTCATTTCCATTCTT
TACATTGTCATGAACTGGATTGATAACCCTCATCTGCAATATTTTCACCCCTAAAATTTTTA
ACAGGGTTTCCTTTTTTTCTCACGACTATTTAAGTTTAGATTGCTCCATTATTAACTGATTA
ATGCACTTTGAAGTTCTCTGGAATTAATTATTTTAACTTGGCCTAGCTTCGACTGTCAAGGT
GGCTGTTATAAATTTGACTTCATTGGCAGTGGATGAAGCCTAAGCCAGCTGAGTCTCTATCA
TAGCTGAACCCTGAGGACAGCCTCATAGCTCATGTATCAGGGACTTTTGCCACATTTCAGAG
GCATAGCATGAACAAGTAATATTAAGCCAAGAATAAGCAGCAGAACCCTGTTCCATATGGAA
AAAAGAAAAACAATTTTTTGTCCCTAATGTTCTTCCTTTTACATCCTGGAACAACAATAAAA
ACATTTTTTTAAACTTGTCTACTGTAAGATACTGCCATCATAAAGCAGAGACTTACATGAGT
GAAAGGGTTGCCTCATCAAGCAGCTCAGTGTAAATGGGGAGGCTAGGCTCTCCCCAGCCCTA
TGGTTTTTTTATTTCATGTACCCCAGGAAATACTGTGTGGTTTCTAAAAGCCCTGGTTGTTA
AAAGTAGGGACTCTGCCTTTTTGTTGGTAGGGAGAAAAAACGCTATTGCTTTGTCTTACAGA
GCGAATGTCTGCCAACTACCCGTTCATTATATAAGTCTGAACTTGGTAATATATGGCTAATG
AAGATTAAGCCCTCTATAAAGACTTCCTGTTGAGGTGAATTCTCATACTGAAATGTAGTTAC
CTACAATATTTACTAGAGATTTATGAAATTAAATTAAGAGATAATGTAAGAAAATACATTTT
TTTTGGTTCTATATAATGCTTCATGATTCATTTAGGGACCTAGAAATATTGTGTGAAAATAT
ATAAATATCACCCAAAAGGCTTTCTGCCCTATATTTTAAAATACAGAATAGTTATATTTGA
AGTAGCCCTGGCCCTAGTTCTATAGGGCTTGGCTATTTAATATTTTTATGGAAGAAGTGTTT
AGTTCTGGAAAAGGTAAATGCTTGTATATATATTTTTGCAGCCTGGGATCTCCCTACTCCAT
TTTTTCCTTTAATTTAAGTGGCCACATGTATATGTCTTCCCTGCTGTGTTAGGAAATGGGG
GCTGGATATCCCAAGAATCAGAGGTTATATAAAAATACTGCAAATAGACCGCAGACATAAAT
ATCTACCAAATGCTATCTTAAATTTTGGTCCAAACTGAACATATGGAAATAGATTTATTGTA
AGTATTTACTTAGAGCTTTTTCTTAAATCTGAACTAACTTGCTTTTAGAAGTCTTTTTCTTT
GTAAGCATTGTAAATGCTAATAAATCC
```

FIG.2

```
ATGGGTAGCCTCACCATGAAATCACAGCTTCAGATCACTGTCATCTCAGCAAAACTTAAGGA
AAATAAGAAGAATTGGTTTGGACCAAGTCCTTACGTAGAGGTCACAGTAGATGGACAGTCAA
AGAAGACAGAAAAATGCAACAACACAAACAGTCCCAAGTGGAAGCAACCCCTTACAGTTATC
GTTACCCCTGTGAGTAAATTACATTTTCGTGTGTGGAGTCACCAGACACTGAAATCTGATGT
TTTGTTGGGAACTGCTGCATTAGATATTTATGAAACATTAAAGTCAAACAATATGAAACTTG
AAGAAGTAGTTGTGACTTTGCAGCTTGGAGGTGACAAAGAGCCAACAGAGACAATAGGAGAC
TTGTCAATTTGTCTTGATGGGCTACAGTTAGAGTCTGAAGTTGTTACCAATGGTGAAACTAC
ATGTTCAGAAAGTGCTTCTCAGAATGATGATGGCTCCAGATCCAAGGATGAAACAAGAGTGA
GCACAAATGGATCAGATGACCCTGAAGATGCAGGAGCTGGTGAAAATAGGAGAGTCAGTGGG
AATAATTCTCCATCACTCTCAAATGGTGGTTTTAAACCTTCTAGACCTCCAAGACCTTCACG
ACCACCACCACCCACCCCACGTAGACCAGCATCTGTCAATGGTTCACCATCTGCCACTTCTG
AAAGTGATGGGTCTAGTACAGGCTCTCTGCCGCCGACAAATACAAATACAAATACATCTGAA
GGAGCAACATCTGGATTAATAATTCCTCTTACTATATCTGGAGGCTCAGGCCCTAGGCCATT
AAATCCTGTAACTCAAGCTCCCTTGCCACCTGGTTGGGAGCAGAGAGTGGACCAGCACGGGC
GAGTTTACTATGTAGATCATGTTGAGAAAGAACAACATGGGATAGACCAGAACCTCTACCT
CCTGGCTGGGAACGGCGGGTTGACAACATGGGACGTATTTATTATGTTGACCATTTCACAAG
AACAACAACGTGGCAGAGGCCAACACTGGAATCCGTCCGGAACTATGAACAATGGCAGCTAC
AGCGTAGTCAGCTTCAAGGAGCAATGCAGCAGTTTAACCAGAGATTCATTTATGGGAATCAA
GATTTATTTGCTACATCACAAAGTAAAGAATTTGATCCTCTTGGTCCATTGCCACCTGGATG
GGAGAAGAGAACAGACAGCAATGGCAGAGTATATTTCGTCAACCACAACACACGAATTACAC
AATGGGAAGACCCCAGAAGTCAAGGTCAATTAAATGAAAGCCCTTACCTGAAGGTTGGGAA
ATGAGATTCACAGTGGATGGAATTCCATATTTTGTGGACCACAATAGAAGAACTACCACCTA
TATAGATCCCCGCACAGGAAAATCTGCCCTAGACAATGGACCTCAGATAGCCTATGTTCGGG
ACTTCAAAGCAAAGGTTCAGTATTTCCGGTTCTGGTGTCAGCAACTGGCCATGCCACAGCAC
ATAAAGATTACAGTGACAAGAAAAACATTGTTTGAGGATTCCTTTCAACAGATAATGAGCTT
CAGTCCCCAAGATCTGCGAAGACGTTTGTGGGTGATTTTCCAGGAGAAGAAGGTTTAGATT
ATGGAGGTGTAGCAAGAGAATGGTTCTTTCTTTTGTCACATGAAGTGTTGAACCCAATGTAT
TGCCTGTTTGAATATGCAGGGAAGGATAACTACTGCTTGCAGATAAACCCCGCTTCTTACAT
CAATCCAGATCACCTGAAATATTTTCGTTTTATTGGCAGATTTATTGCCATGGCTCTGTTCC
ATGGGAAATTCATAGACACGGGTTTTTCTTTACCATTCTATAAGCGTATCTTGAACAAACCA
GTTGGACTCAAGGATTTAGAATCTATTGATCCAGAATTTTACAATTCTCTCATCTGGGTTAA
GGAAAACAATATTGAGGAATGTGATTTGGAAATGTACTTCTCCGTTGACAAAGAAATTCTAG
GTGAAATTAAGAGTCATGATCTGAAACCTAATGGTGGCAATATTCTTGTAACAGAAGAAAT
AAAGAGGAATACATCAGAATGGTAGCTGAGTGGAGGTTGTCTCGAGGTGTTGAAGAACAGAC
ACAAGCTTTCTTTGAAGGCTTTAATGAAATTCTTCCCCAGCAATATTTGCAATACTTTGATG
CAAAGGAATTAGAGGTCCTTTTATGTGGAATGCAAGAGATTGATTTGAATGACTGGCAAAGA
CATGCCATCTACCGTCATTATGCAAGGACCAGCAAACAAATCATGTGGTTTTGGCAGTTTGT
TAAAGAAATTGATAATGAGAAGAGAATGAGACTTCTGCAGTTTGTTACTGGAACCTGCCGAT
TGCCAGTAGGAGGATTTGCTGATCTCATGGGGAGCAATGGACCACAGAAATTCTGCATTGAA
AAAGTTGGGAAGAAAATTGGCTACCCAGAAGTCATACCTGTTTTAATCGCCTGGACCTGCC
ACCATACAAGAGCTATGAGCAACTGAAGGAAAGCTGTTGTTTGCCATAGAAGAAACAGAAG
GATTTGGACAAGAGTAA
```

FIG.3

MGSLTMKSQLQITVISAKLKENKKNWFGPSPYVEVTVDGQSKKTEKCNNTNSPKWKQPLTVI
VTPVSKLHFRVWSHQTLKSDVLLGTAALDIYETLKSNNMKLEEVVVTLQLGGDKEPTETIGD
LSICLDGLQLESEVVTNGETTCSESASQNDDGSRSKDETRVSTNGSDDPEDAGAGENRRVSG
NNSPSLSNGGFKPSRPPRPSRPPPPTPRRPASVNGSPSATSESDGSSTGSLPPTNTNTNTSE
GATSGLIIPLTISGGSGPRPLNPVTQAPLPPGWEQRVDQHGRVYYVDHVEKRTTWDRPEPLP
PGWERRVDNMGRIYYVDHFTRTTTWQRPTLESVRNYEQWQLQRSQLQGAMQQFNQRFIYGNQ
DLFATSQSKEFDPLGPLPPGWEKRTDSNGRVYFVNHNTRITQWEDPRSQGQLNEKPLPEGWE
MRFTVDGIPYFVDHNRRTTTYIDPRTGKSALDNGPQIAYVRDFKAKVQYFRFWCQQLAMPQH
IKITVTRKTLFEDSFQQIMSFSPQDLRRRLWVIFPGEEGLDYGGVAREWFFLLSHEVLNPMY
CLFEYAGKDNYCLQINPASYINPDHLKYFRFIGRFIAMALFHGKFIDTGFSLPFYKRILNKP
VGLKDLESIDPEFYNSLIWVKENNIEECDLEMYFSVDKEILGEIKSHDLKPNGGNILVTEEN
KEEYIRMVAEWRLSRGVEEQTQAFFEGFNEILPQQYLQYFDAKELEVLLCGMQEIDLNDWQR
HAIYRHYARTSKQIMWFWQFVKEIDNEKRMRLLQFVTGTCRLPVGGFADLMGSNGPQKFCIE
KVGKENWLPRSHTCFNRLDLPPYKSYEQLKEKLLFAIEETEGFGQE

FIG.4

MGSLTMKSQLQITVISAKLKENKKNWFGPSPYVEVTVDGQSKKTEKCNNTNSPKWKQPLTVI
VTPTSKLCFRVWSHQTLKSDVLLGTAGLDIYETLKSNNMKLEEVVMTLQLVGDKEPTETMGD
LSVCLDGLQVEAEVVTNGETSCSESTTQNDDGCRTRDDTRVSTNGSEDPEVAASGENKRANG
NNSPSLSNGGFKPSRPPRPSRPPPPTPRRPASVNGSPSTNSDSDGSSTGSLPPTNTNVNTST
SEGATSGLIIPLTISGGSGPRPLNTVSQAPLPPGWEQRVDQHGRVYYVDHVEKRTTWDRPEP
LPPGWERRVDNMGRIYYVDHFTRTTTWQRPTLESVRNYEQWQLQRSQLQGAMQQFNQRFIYG
NQDLFATSQNKEFDPLGPLPPGWEKRTDSNGRVYFVNHNTRITQWEDPRSQGQLNEKPLPEG
WEMRFTVDGIPYFVDHNRRATTYIDPRTGKSALDNGPQIAYVRDFKAKVQYFRFWCQQLAMP
QHIKITVTRKTLFEDSFQQIMSFSPQDLRRRLWVIFPGEEGLDYGGVAREWFFLLSHEVLNP
MYCLFEYAGKDNYCLQINPASYINPDHLKYFRFIGRFIAMALFHGKFIDTGFSLPFYKRILN
KPVGLKDLESIDPEFYNSLIWVKENNIEECGLEMYFSVDKEILGEIKSHDLKPNGGNILVTE
ENKEEYIRMVAEWRLSRGVEEQTQAFFEGFNEILPQQYLQYFDAKELEVLLCGMQEIDLNDW
QRHAIYRHYTRTSKQIMWFWQFVKEIDNEKRMRLLQFVTGTCRLPVGGFADLMGSNGPQKFC
IEKVGKENWLPRSHTCFNRLDLPPYKSYEQLKEKLLFAIEETEGFGQE

FIG.5

SEQ ID NO:4  MGSLTMKSQLQITVISAKLKENKKNWFGPSPYVEVTVDGQSKKTEKCNNT
SEQ ID NO:3  MGSLTMKSQLQITVISAKLKENKKNWFGPSPYVEVTVDGQSKKTEKCNNT

SEQ ID NO:4  NSPKWKQPLTVIVTPTSKLCFRVWSHQTLKSDVLLGTAGLDIYETLKSNN
SEQ ID NO:3  NSPKWKQPLTVIVTPVSKLHFRVWSHQTLKSDVLLGTAALDIYETLKSNN

SEQ ID NO:4  MKLEEVVMTLQLVGDKEPTETMGDLSVCLDGLQVEAEVVTNGETSCSEST
SEQ ID NO:3  MKLEEVVV TLQLGGDKEPTETI GDLSI CLDGLQ LESEVVTNGETTCSESA

SEQ ID NO:4  TQNDDGCRTRDDTRVSTNGSEDPEVAASGENKRANGNNSPSLSNGGFKPS
SEQ ID NO:3  SQNDDGS RSKDE TRVSTNGSDDPEDAGAGENRRVSGNNSPSLSNGGFKPS

SEQ ID NO:4  RPPRPSRPPPPTPRRPASVNGSPSTNSDSDGSSTGSLPPTNTNVNTSTSE
SEQ ID NO:3  RPPRPSRPPPPTPRRPASVNGSPSATSE SDGSSTGSLPPTNTNTNT - -SE

SEQ ID NO:4  GATSGLIIPLTISGGSGPRPLNTVSQAPLPPGWEQRVDQHGRVYYVDHVE
SEQ ID NO:3  GATSGLIIPLTISGGSGPRPLNPVTQAPLPPGWEQRVDQHGRVYYVDHVE

SEQ ID NO:4  KRTTWDRPEPLPPGWERRVDNMGRIYYVDHFTRTTTWQRPTLESVRNYEQ
SEQ ID NO:3  KRTTWDRPEPLPPGWERRVDNMGRIYYVDHFTRTTTWQRPTLESVRNYEQ

SEQ ID NO:4  WQLQRSQLQGAMQQFNQRFIYGNQDLFATSQNKEFDPLGPLPPGWEKRTD
SEQ ID NO:3  WQLQRSQLQGAMQQFNQRFIYGNQDLFATSQSKEFDPLGPLPPGWEKRTD

SEQ ID NO:4  SNGRVYFVNHNTRITQWEDPRSQGQLNEKPLPEGWEMRFTVDGIPYFVDH
SEQ ID NO:3  SNGRVYFVNHNTRITQWEDPRSQGQLNEKPLPEGWEMRFTVDGIPYFVDH

SEQ ID NO:4  NRRATTYIDPRTGKSALDNGPQIAYVRDFKAKVQYFRFWCQQLAMPQHIK
SEQ ID NO:3  NRRTTTYIDPRTGKSALDNGPQIAYVRDFKAKVQYFRFWCQQLAMPQHIK

SEQ ID NO:4  ITVTRKTLFEDSFQQIMSFSPQDLRRRLWVIFPGEEGLDYGGVAREWFFL
SEQ ID NO:3  ITVTRKTLFEDSFQQIMSFSPQDLRRRLWVIFPGEEGLDYGGVAREWFFL

SEQ ID NO:4  LSHEVLNPMYCLFEYAGKDNYCLQINPASYINPDHLKYFRFIGRFIAMAL
SEQ ID NO:3  LSHEVLNPMYCLFEYAGKDNYCLQINPASYINPDHLKYFRFIGRFIAMAL

SEQ ID NO:4  FGHKFIDTGFSLPFYKRILNKPVGLKDLESIDPEFYNSLIWVKENNIEEC
SEQ ID NO:3  FHGKFIDTGFSLPFYKRILNKPVGLKDLESIDPEFYNSLIWVKENNIEEC

SEQ ID NO:4  GLEMYFSVDKEILGEIKSHDLKPNGGNILVTEENKEEYIRMVAEWRLSRG
SEQ ID NO:3  DLEMYFSVDKEILGEIKSHDLKPNGGNILVTEENKEEYIRMVAEWRLSRG

SEQ ID NO:4  VEEQTQAFFEGFNEILPQQYLQYFDAKELEVLLCGMQEIDLNDWQRHAIY
SEQ ID NO:3  VEEQTQAFFEGFNEILPQQYLQYFDAKELEVLLCGMQEIDLNDWQRHAIY

SEQ ID NO:4  RHTTRSKQIMWFWQFVKEIDNEKRMRLLQFVTGTDRLPVGGLADLMGSN
SEQ ID NO:3  RHYARSKQIMWFWQFVKEIDNEKRMRLLQFVTGTDRLPVGGLADLMGSN

SEQ ID NO:4  GPQKFCIEKVGKENWLPRSHTCFNRLDLPPYKSFEQLKEKLLFAIEETEG
SEQ ID NO:3  GPQKFCIEKVGKENWLPRSHTCFNRLDLPPYKSFEQLKEKLLFAIEETEG

†
SEQ ID NO:4  FGQE
SEQ ID NO:3  FGQE

FIG.7 sense 5'- ATGGGTAGCCTCACCATGAAA -3' (SEQ ID NO:5)

antisense 5'- TTACTCTTGTCCAAATCCTTC -3' (SEQ ID NO:6)

FIG.9

MQIFVKTLTGKTITLEVEPSDTIENVKAKIQDKEGIPPDQQRLIFAGKQLEDGRTLSDYNIQ
KESTLHLVLRLRGGAKKRKKKSYTTPKKNKHKRKKVKLAVLKYYKVDENGKISRLRRECPSD
ECGAGVFMASHFDRHYCGKCCLTYCFNKPEDK

FIG.10

MQIFVKTLTGKTITLEVEPSDTIENVKAKIQDKEGIPPDQQRLIFAGKQLEDGRTLSDYNIQ
KESTLHLVLRLRGG

FIG.11

ATGCAGATTTTCGTGAAAACCCTTACGGGGAAGACCATCACCCTCGAGGTTGAACCCTCGGA
TACGATAGAAAATGTAAAGGCCAAGATCCAGGATAAGGAAGGAATTCCTCCTGATCAGCAGA
GACTGATCTTTGCTGGCAAGCAGCTGGAAGATGGACGTACTTTGTCTGACTACAATATTCAA
AAGGAGTCTACTCTTCATCTTGTGTTGAGACTTCGTGGTGGTGCTAAGAAAAGGAAGAAGAA
GTCTTACACCACTCCCAAGAAGAATAAGCACAAGAGAAAGAAGGTTAAGCTGGCTGTCCTGA
AATATTATAAGGTGGATGAGAATGGCAAAATTAGTCGCCTTCGTCGAGAGTGCCCTTCTGAT
GAATGTGGTGCTGGGGTGTTTATGGCAAGTCACTTTGACAGACATTATTGTGGCAAATGTTG
TCTGACTTACTGTTTCAACAAACCAGAAGACAAGTAA

FIG.12

```
ATGTCCAGCTCGCCGCTGTCCAAGAAACGTCGCGTGTCCGGGCCTGATCCAAAGCCGGGTTC
TAACTGCTCCCCTGCCCAGTCCGTGTTGTCCGAAGTGCCCTCGGTGCCAACCAACGGAATGG
CCAAGAACGGCAGTGAAGCAGACATAGACGAGGGCCTTTACTCCCGGCAGCTGTATGTGTTG
GGCCATGAGGCAATGAAGCGGCTCCAGACATCCAGTGTCCTGGTATCAGGCCTGCGGGGCCT
GGGCGTGGAGATCGCTAAGAACATCATCCTTGGTGGGGTCAAGGCTGTTACCCTACATGACC
AGGGCACTGCCCAGTGGGCTGATCTTTCCTCCCAGTTCTACCTGCGGGAGGAGGACATCGGT
AAAAACCGGGCCGAGGTATCACAGCCCCGCCTCGCTGAGCTCAACAGCTATGTGCCTGTCAC
TGCCTACACTGGACCCCTCGTTGAGGACTTCCTTAGTGGTTTCCAGGTGGTGGTGCTCACCA
ACACCCCCCTGGAGGACCAGCTGCGAGTGGGTGAGTTCTGTCACAACCGTGGCATCAAGCTG
GTGGTGGCAGGCACGCGGGGCCTGTTTGGGCAGCTCTTCTGTGACTTTGGAGAGGAAATGAT
CCTCACAGATTCCAATGGGGAGCAGCCACTCAGTGCTATGGTTTCTATGGTTACCAAGGACA
ACCCCGGTGTGGTTACCTGCCTGGATGAGGCCCGACACGGGTTTGAGAGCGGGGACTTTGTC
TCCTTTTCAGAAGTACAGGGCATGGTTGAACTCAACGGAAATCAGCCCATGGAGATCAAAGT
CCTGGGTCCTTATACCTTTAGCATCTGTGACACCTCCAACTTCTCCGACTACATCCGTGGAG
GCATCGTCAGTCAGGTCAAAGTACCTAAGAAGATTAGCTTTAAATCCTTGGTGGCCTCACTG
GCAGAACCTGACTTTGTGGTGACGGACTTCGCCAAGTTTTCTCGCCCTGCCCAGCTGCACAT
TGGCTTCCAGGCCCTGCACCAGTTCTGTGCTCAGCATGGCCGGCCACCTCGGCCCCGCAATG
AGGAGGATGCAGCAGAACTGGTAGCCTTAGCACAGGCTGTGAATGCTCGAGCCCTGCCAGCA
GTGCAGCAAAATAACCTGGACGAGGACCTCATCCGGAAGCTGGCATATGTGGCTGCTGGGGA
TCTGGCACCCATAAACGCCTTCATTGGGGCCTGGCTGCCCAGGAAGTCATGAAGGCCTGCT
CCGGGAAGTTCATGCCCATCATGCAGTGGCTATACTTTGATGCCCTTGAGTGTCTCCCTCAG
GACAAAGAGGTCCTCACAGAGGACAAGTGCCTCCAGCGCCAGAACCGTTATGACGGGCAAGT
GGCTGTGTTTGGCTCAGACCTGCAAGAGAAGCTGGGCAAGCAGAAGTATTTCCTGGTGGGTG
CGGGGGCCATTGGCTGTGAGCTGCTCAAGAACTTTGCCATGATTGGGCTGGGCTGCGGGGAG
GGTGGAGAAATCATCGTTACAGACATGGACACCATTGAGAAGTCAAATCTGAATCGACAGTT
TCTTTTCCGGCCCTGGGATGTCACGAAGTTAAAGTCTGACACGGCTGCTGCAGCTGTGCGCC
AAATGAATCCACATATCCGGGTGACAAGCCACCAGAACCGTGTGGGTCCTGACACGGAGCGC
ATCTATGATGACGATTTTTTCCAAAACCTAGATGGCGTGGCCAATGCCCTGGACAACGTGGA
TGCCCGCATGTACATGGACCGCCGCTGTGTCTACTACCGGAAGCCACTGCTGGAGTCAGGCA
CACTGGGCACCAAAGGCAATGTGCAGGTGGTGATCCCCTTCCTGACAGAGTCGTACAGTTCC
AGCCAGGACCCACCTGAGAAGTCCATCCCCATCTGTACCCTGAAGAACTTCCCTAATGCCAT
CGAGCACACCCTGCAGTGGGCTCGGGATGAGTTTGAAGGCCTCTTCAAGCAGCCAGCAGAAA
ATGTCAACCAGTACCTCACAGACCCCAAGTTTGTGGAGCGAACACTGCGGCTGGCAGGCACT
CAGCCCTTGGAGGTGCTGGAGGCTGTGCAGCGCAGCCTGGTGCTGCAGCGACCACAGACCTG
GGCTGACTGCGTGACCTGGGCCTGCCACCACTGGCACACCCAGTACTCGAACAACATCCGGC
AGCTGCTGCACAACTTCCCTCCTGACCAGCTCACAAGCTCAGGAGCGCCGTTCTGGTCTGGG
CCCAAACGCTGTCCACACCCGCTCACCTTTGATGTCAACAATCCCCTGCATCTGGACTATGT
GATGGCTGCTGCCAACCTGTTTGCCCAGACCTACGGGCTGACAGGCTCTCAGGACCGAGCTG
CTGTGGCCACATTCCTGCAGTCTGTGCAGGTCCCCGAATTCACCCCCAAGTCTGGCGTCAAG
ATCCATGTTTCTGACCAGGAGCTGCAGAGCGCCAATGCCTCTGTTGATGACAGTCGTCTAGA
GGAGCTCAAAGCCACTCTGCCCAGCCCAGACAAGCTCCCTGGATTCAAGATGTACCCCATTG
ACTTTGAGAAGGATGATGACAGCAACTTTCATATGGATTTCATCGTGGCTGCATCCAACCTC
CGGGCAGAAAACTATGACATTCCTTCTGCAGACCGGCACAAGAGCAAGCTGATTGCAGGGAA
GATCATCCCAGCCATTGCCACGACCACAGCAGCCGTGGTTGGCCTTGTGTCTGGAGCTGT
ACAAGGTTGTGCAGGGGCACCGACAGCTTGACTCCTACAAGAATGGTTTCCTCAACTTGGCC
CTGCCTTTCTTTGGTTTCTCTGAACCCCTTGCCGCACCACGTCACCAGTACTATAACCAAGA
GTGGACATTGTGGGATCGCTTTGAGGTACAAGGGCTGCAGCCTAATGGTGAGGAGATGACCC
TCAAACAGTTCCTCGACTATTTTAAGACAGAGCACAAATTAGAGATCACCATGCTGTCCCAG
GGCGTGTCCATGCTCTATTCCTTCTTCATGCCAGCTGCCAAGCTCAAGGAACGGTTGGATCA
GCCGATGACAGAGATTGTGAGCCGTGTGTCGAAGCGAAAGCTGGGCCGCCACGTGCGGGCGC
```

TGGTGCTTGAGCTGTGCTGTAACGACGAGAGCGGCGAGGATGTCGAGGTTCCCTATGTCCGA
TACACCATCCGCTGA

FIG.13

```
ATGGCGCTGAAACGGATTAATAAGGAACTTAGTGATTTGGCCCGTGACCCTCCAGCACAATG
TTCTGCAGGTCCAGTTGGAGATGACATGTTTCATTGGCAAGCCACAATTATGGGACCTAATG
ACAGCCCATATCAAGGTGGTGTATTCTTTTTGACAATTCATTTTCCTACAGACTACCCCTTC
AAACCACCTAAGGTTGCATTTACAACAAGAATTTATCATCCAAATATTAACAGTAATGGCAG
CATTTGTCTTGATATTCTAAGATCACAGTGGTCTCCTGCTTTAACTATTTCTAAAGTTCTTT
TATCCATTTGTTCACTGCTATGTGATCCAAACCCAGATGACCCCTAGTGCCAGAGATTGCA
CGGATCTATAAAACAGACAGAGACAAGTACAACAGAATATCTCGGGAATGGACTCAGAAGTA
TGCCATGTGA
```

HUMAN E3 UBIQUITIN PROTEIN LIGASE

Applicants herein claim priority under Title 35 USC § 119(e) from the Provisional Application, HUMAN E3 UBIQUITIN PROTEIN LIGASE, Ser. No. 60/073,839, filed Feb. 5, 1998, which is incorporated herein by reference.

FIELD OF THE INVENTION

The present invention relates to nucleic acid and amino acid sequences of a novel human E3 ubiquitin protein ligase and to the use of these sequences to identify compounds that modulate the biological activity of the native biomolecule as well as modulate protein degradation or selective proteolysis and/or otherwise modulate physiological conditions associated with aberrant ubiquitin dependent proteolysis in human physiology. The invention is also related to the diagnosis, study, prevention, and treatment of pathophysiological disorders related to or mediated by the novel human E3 ubiquitin protein ligase.

BACKGROUND OF THE INVENTION

Three major proteolytic pathways (lysosomal, calcium-dependent, and the ATP-dependent pathways) exist in eukaryotic cells. The ATP-dependent pathway has long been known orchestrate specific degradation of native proteins. Recently it has become clear that the ATP-dependent ubiquitin mediated intracellular pathway is responsible for selective degradation of intact biomolecules as an efficiently evolved mechanism to adapt cellular physiology to the needs of the organism. Proteolysis is a powerful means of regulation due to the speed and irreversibility which enables the cell to rapidly eliminate or reduce the functional level of a particular biological molecule. See, e.g., Jentsch, S., et al., *Selective Protein Degradation: A Journey's end Within the Proteasome*, Cell, 82:129 (1995). The critical role of ubiquitin-dependent proteolysis has steadily become increasingly clear, for example, in the normal degradation of oncoproteins and tumor suppressers in cell cycle control as well as in stress response and the immune system. Hochstrasser, M., Current Biology, 4:1024 (1992); Deshaies, R. J., Trends Cell Biol., 5:428 (1995); Hilt, W., et al., Trends Biol. Sci., 21:96 (1996).

Ubiquitin is a heat-stable 76-amino acid biomolecule considered to be the most highly conserved protein known. Selective protein degradation via the ubiquitin pathway generally involves tagging of the target protein (substrate) by covalent attachment of multiple molecules of ubiquitin, and degradation of the target by the 26 S proteasome complex. Proteins are marked for direction to the proteasome via the covalent addition of branched polyubiquitin chains to the α-amino group of one or more surface lysines. The amide linkage of ubiquitin to a substrate protein is generally carried out by three classes of accessory enzymes in a sequential reaction. Ubiquitin activating enzymes (E1) activate ubiquitin by forming a high energy thiol ester intermediate. Activation of the C-terminal Gly of ubiquitin by E1, is followed by the activity of a ubiquitin conjugating enzyme E2 which serves as a carrier of the activated thiol ester form of ubiquitin during the transfer of ubiquitin directly to the third enzyme, E3 ubiquitin protein ligase. E3 ubiquitin protein ligase is responsible for the final step in the conjugation process which results in the formation of an isopeptide bond between the activated Gly residue of ubiquitin, and an (α-NH group of a Lys residue in the substrate or a previously conjugated ubiquitin moiety. See, e.g., Hochstrasser, M., *Ubiquitin-Dependent Protein Degradation*, Annu. Rev. Genet., 30:405 (1996).

In a reconstituted system, for example, all three categories of affinity purified enzymes (E1, E2, and E3) are required for the breakdown of $^{125}$I-albumin to acid-soluble material in the presence of ubiquitin and ATP. Sears, C., et al., *NF-kB p105 Processing Via the Ubiquitin-Proteasome Pathway*, J Biol Chem., 273:1409 (1998). The high specificity of the ubiquitin selective-destruction pathway is predicted to allow the development of new classes of highly potent and selective low molecular weight enzyme inhibitors targeting particular members of the ubiquitin pathway that control the intracellular levels of a wide range of important regulatory proteins. Rolfe, M., et al., *The Ubiquitin-Mediated Proteolytic Pathway as a Therapeutic Area*, J. Mol. Med. 75:5–17 (1997).

Compelling evidence has been presented that implicates ubiquitination in the turnover of the tumor supressor protein, p53, cell cycle regulators cyclin A and cyclin B, the kinase c-mos, the cystic fibrosis transmembrane conductance regulator, the DNA repair protein $O^6$-methylguanine-DNA methyl transferase, the transcriptional co-activator p300, the transcription factors c-jun, c-fos, IκB/NFκB, the transcription factors c-myc, DP1, and E2F, the regulatory subunit of cAMP-dependent protein kinase, receptors for peptide growth factors, estradiol receptor, as well as oncoprotein E1A. Moreover, as a corollary, pharmacological intervention which alters the half-lives of these cellular proteins is expected to have significant value in wide therapeutic potential, particularly in the areas of autoimmune disease, inflammation, cancer, as well as other proliferative disorders. Rolfe, M., et al., *The Ubiquitin-Mediated Proteolytic Pathway as a Therapeutic Area*, J. Mol. Med., 75:5 (1997).

E3 ubiquitin protein ligase, as the final player in the ubiquitination process, is responsible for target specificity of ubiquitin-dependent proteolysis. A number of E3 ubiquitin-protein ligases have previously been identified. See, e.g., D'Andrea, A. D., et al., Nature Genetics, 18:97 (1998); Gonen, H., et al., *Isolation, Characterization, and Purification of a Novel Ubiquitin-Protein Ligase, E3—Targeting of Protein Substrates via Multiple and Distinct Recognition Signals and Conjugating Enzymes*, J. Biol. Chem., 271:302 (1996); Scheffner, M., et al., *The HPV-16 E6 and E6-AP Complex Functions as a Ubiquitin-Protein Ligase in the Ubiquitination of p53*, Cell, 75:495 (1993); Huibregtse, J. M., et al., *A Family of Proteins Structurally and Functionally Related to the E6-AP Ubiquitin Protein Ligase*, PNAS, 92:2563 (1995); Staub, O., et al., *WW Domains of Nedd4 Bind to the Proline-Rich PY Motifs in the Epithelial Na+ Channel Deleted in Liddles Syndrome*, EMBO, 15:2371 (1996) [the substrate specificity is determined by the E3 ligase]; Siepmann, T. J., et al., *Evidence for Stable, Exchangeable E1/E2/E3 Ubiquitin Conjugation Complexes at Physiological Concentrations*, FASEB J., 10:2324 (1996).

Other E3 ligases have been extensively evaluated in *S. cerevisiae* and in cell-free systems using engineered proteins as test substrates. Weissman, A. M., *Regulating Protein Degradation by Ubiquitination, Review Immunology Today*, 18(4):189 (1997); Sudakin, V., et al., Mol. Biol. Cell, 6:185 (1995); Stancovski, I., et al., Mol. Cell. Biol., 15:7106 (1995); King, R. W., et al., Cell, 81:279 (1995); Chen, Z. J., et al., Cell, 84:853 (1996); Orian, A., et al., J. Biol. Chem., 170:21707 (1995); Varshavsky, A., et al., Cell, 69:725 (1992); Hershko, A., et al., Annu. Rev. Biochem., 61:761 (1992); Ciechanover, A., Cell, 7:13 (1994).

Perry et al., recently identified a single gene which encodes a murine E3 ubiquitin protein ligase of the Hect family, disruption of which is demonstrated to cause an inflammatory phenotype of the mouse as well as enhanced epithelial and haematopoietic cell growth. Perry, W. L., et al., Nature Genetics, 18:143 (1998). The murine E3 results reported by Perry et al indicate the specific ubiquitin-dependent proteolysis is an important mediator in the immune response as well as haematopoietic cell growth in vivo. Moreover, it is recently set forth that modulators of the E3 ubiquitin protein ligase are likely to have significant therapeutic potential, inter alia, as novel anti-inflammatory agents as well as entities to promote wound-healing. D'Andrea, A. D., et al., Nature Genetics, 18:97 (1998); Perry, W. L., et al., Nature Genetics, 18:143 (1998).

However, the previously reported E3 ubiquitin protein ligase is a murine isolate. The availability of an analogous functional human homolog will be ideal for the identification of compounds which modulate the specific biological activity of the E3 protein ligase and, as a corollary, modulate the physiological conditions associated with aberrant ubiquitin dependent proteolysis in human physiology. The availability of an analogous functional human homolog will also be ideal for the diagnosis, study, prevention, and treatment of pathophysiological disorders related to the biological molecule.

SUMMARY OF THE INVENTION

The present invention is directed to an isolated and purified polynucleotide molecule, which encodes a human E3 ubiquitin protein ligase, or a biologically-effective fragment thereof comprising a nucleic acid sequence encoding the polypeptide having the sequence substantially as depicted in SEQ ID NO:3 or a pharmacologically acive fragment thereof. Isolated and purified polynucleotides of the present invention include but are not limited to SEQ ID NO:1 (human E3 ubiquitin protein ligase cDNA) and SEQ ID NO:2 (human E3 ubiquitin protein ligase structural coding region).

In addition, the current invention is directed to a purified polypeptide comprising the amino acid sequence substantially as depicted in SEQ ID NO:3.

The invention is further directed to a host cell containing an expression vector for expression of a human E3 ubiquitin protein ligase polypeptide, wherein said vector contains a polynucleotide comprising a nucleic acid sequence encoding the polypeptide of a human E3 ubiquitin protein ligase having the sequence substantially as depicted in SEQ ID NO:3 or a pharmacologically active fragment thereof. The invention is also directed to a method for producing a human E3 ubiquitin protein ligase polypeptide having the amino acid sequence substantially as depicted in SEQ ID NO:3 by culturing said host cell under conditions suitable for the expression of said polypeptide, and recovering said polypeptide from the host cell culture.

The instant invention is further directed to a method of identifying compounds that modulate the biological activity of a human E3 ubiquitin protein ligase, comprising:
(a) combining a candidate compound modulator of human E3 ubiquitin protein ligase biological activity with a human E3 ubiquitin protein ligase polypeptide having the sequence substantially as depicted in SEQ ID NO:3, and
(b) measuring an effect of the candidate compound modulator on the biological activity.

The instant invention is further directed to a method of identifying compounds that modulate the pharmacological activity of a human E3 ubiquitin protein ligase, comprising:
(a) combining a candidate compound modulator of human E3 ubiquitin protein ligase pharmacological activity with a host-cell expressing a human E3 ubiquitin protein ligase polypeptide having the sequence substantially as depicted in SEQ ID NO:3, and
(b) measuring an effect of the candidate compound modulator on the pharmacological activity.

The present invention is also directed to active compounds identified by means of the aforementioned methods, wherein said compounds modulate the biological and/or pharmacological activity of a human E3 ubiquitin protein ligase.

The invention is further directed to an antisense polynucleotide molecule comprising substantially the complement of SEQ ID NO:1 or a biologically-effective portion thereof, or SEQ ID NO:2 or a biologically-effective portion thereof, as well as a method for inhibiting the expression of a human E3 ubiquitin protein ligase comprising administering an effective amount of the antisense molecule.

The current invention is also drawn toward an antibody specific for a purified polypeptide comprising the amino acid sequence substantially as depicted in SEQ ID NO:3, as well as a diagnostic composition for the identification of a polypeptide sequence comprising the amino acid sequence substantially as depicted in SEQ ID NO:3.

BRIEF DESCRIPTION OF THE FIGURES

FIG. 1 displays SEQ ID NO:1 which is a 5359 base cDNA nucleic acid sequence which encodes the novel human E3 ubiquitin protein ligase described herein.

FIG. 2 displays SEQ ID NO:2 which is a 2559 base translated structural coding region, ATG to TAA (Ochre), of the cDNA nucleic acid sequence which encodes the novel human E3 ubiquitin protein ligase (human homolog of the murine itchy locus; Perry, W. L., et al., Nature Genetics, 18:143 (1998)).

FIG. 3 displays SEQ ID NO:3 which is a 852 amino acid residue sequence of the human E3 ubiquitin protein ligase homolog described herein.

FIG. 4 shows SEQ ID NO:4 which is the 854 amino acid residue sequence of the murine E3 ubiquitin protein ligase (mapped to itchy locus). Perry, W. L., et al., Nature Genetics, 18:143 (1998); Hustad, C. M., et al., Genetics, 140:255 (1995).

FIG. 5 displays a comparison alignment between the amino acid residue sequence of the novel human E3 ubiquitin protein ligase homolog described herein (SEQ ID NO:3), and the amino acid residue sequences of the murine E3 ubiquitin protein ligase (SEQ ID NO:4).

FIG. 7 displays PCR primers, SEQ ID NO:5 and SEQ ID NO:6, which can be used to amplify the 2559 bp coding region (SEQ ID NO:2) of the novel human E3 ubiquitin protein ligase from human tissue.

FIG. 9 displays SEQ ID NO:7 which is the 156 amino acid precursor peptide to the mature 76 amino acid residue sequence of human ubiquitin. Lund P. K., et al., J. Biol. Chem., 260:7609 (1985).

FIG. 10 displays SEQ ID NO:8 which is the mature 76 amino acid residue sequence of native human ubiquitin (positions 1–76 of SEQ ID NO:7). Lund P. K., et al., J. Biol. Chem., 260:7609 (1985).

FIG. 11 displays SEQ ID NO:9 which is the 471 base translated structural coding region, ATG to TAA (Ochre), of the cDNA nucleic acid sequence which encodes the 156 amino acid precursor peptide (SEQ ID NO:7) to the mature 76 amino acid residue sequence of native human ubiquitin (positions 1–76 of SEQ ID NO:7). Lund P. K., et al., J. Biol. Chem., 260:7609 (1985).

FIG. 12 displays SEQ ID NO:10 which is the 3177 base translated structural coding region, ATG to TGA (Opal), of the nucleic acid sequence which encodes the previously described 1058 amino acid residue human E1 ubiquitin activating enzyme (Uba1). Ayusawa, D., et al., Cell Struct. Funct., 17:113 (1992).

FIG. 13 displays SEQ ID NO:11 which is the 444 base translated structural coding region, ATG to TGA (Opal), of the nucleic acid sequence which encodes the previously described 147 amino acid residue E2 ubiquitin conjugating enzyme $E2_{17k}$ (Ub10a). Wing S. S., et al., Biochem. J., 305:125 (1995). The human version (Ubc2) is preferred as described by Koken, M., et al., PNAS, 88:8865 (1991).

DETAILED DESCRIPTION OF THE INVENTION

Figure 6:
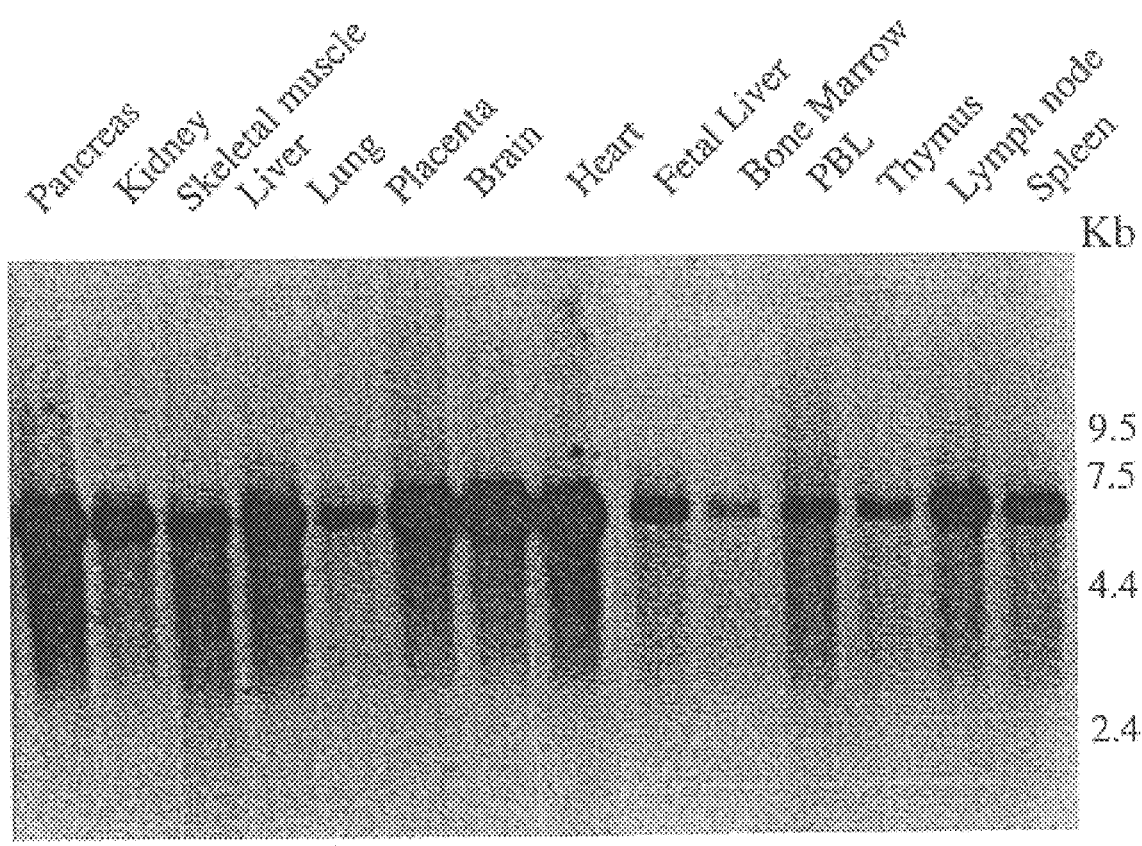
FIG. 6 displays Northern blot analyses of multiple tissues using a nucleic acid probe specific to the human E3 ubiquitin protein ligase coding region described herein (SEQ ID NO:2).

Unless defined otherwise, all technical and scientific terms used herein have the same meaning as is commonly understood by one of skill in the art to which this invention belongs. All publications and patents referred to herein are incorporated by reference.

Nucleic acid sequence as used herein refers to an oligonucleotide, nucleotide or polynucleotide sequence, and fragments or portions thereof, and to DNA or RNA of genomic or synthetic origin which may be double-stranded or single-stranded whether representing the sense or antisense strand. Similarly, amino acid and/or residue sequence as used herein refers to peptide or protein sequences or portions thereof.

Biological activity as used herein refers to the ability of the novel human E3 ubiquitin protein ligase and variations thereof contemplated herein to bind ubiquitin and/or transfer ubiquitin to a substrate under biological conditions.

Pharmacological activity, as used herein in reference to the novel human E3 ubiquitin protein ligase and variations thereof contemplated herein, refers to the ability to modulate protein degradation or selective proteolysis and/or otherwise modulate physiological conditions associated with aberrant ubiquitin dependent proteolysis in human physiology.

The term 'modulation' is used herein to refer to the capacity to either enhance or inhibit the biological activity of a E3 ubiquitin protein ligase. The term "modulation" is also used herein to refer to the pharmacological capacity to to either enhance or inhibit the selective elimination of a biological protein molecule via ubiquitin dependent proteolysis under biological conditions.

Purified as used herein refers to molecules, either nucleic acid or amino acid sequences, that are removed from their natural environment and isolated or separated from at least one other component with which they are naturally associated.

As used herein, a functional derivative of an E3 ubiquitin protein ligase molecular structure or polypeptide disclosed herein is a compound or entity that possesses a biological or pharmacological activity (either functional or structural) that is substantially similar to SEQ ID NO:3. The term "functional derivatives" is intended to include the "fragments," "variants," "degenerate variants," "analogs" and "homologues", and to "chemical derivatives". The term "variant" is meant to refer to a molecule substantially similar in structure and function to either an entire E3 ubiquitin protein ligase molecule or to a fragment thereof. A molecule is "substantially similar" to an E3 ubiquitin protein ligase polypeptide if both molecules have substantially similar structures or if both molecules possess similar pharmacological or biological activity. The term "analog" refers to a molecule substantially similar in function to either an entire native polypeptide, or to a C-terminal fragment thereof.

Substantially as depicted as used herein refers to functional derivative proteins, variant peptides and DNA sequences that may have changes but perform substantially the same biochemical function in substantially the same way.

Biologically active fragment or pharmacologically active fragment as used herein includes peptides which have been truncated with respect to the N- or C-termini, or both; or the corresponding 5' or 3' end, or both, of the corresponding polynucleotide coding region, which fragments perform substantially the same function or encode peptides which perform substantially the same function in substantially the same way. The term "biologically active" or "pharmacologically active" also refers to the activity of a homolog or analog entity having structural, regulatory or biochemical functions substantially the same as the naturally occurring entity.

Expression vector as used herein refers to nucleic acid vector constructions which have components to direct the expression of heterologous protein coding regions including coding regions of the present invention through accurate transcription and translation in host cells. Expression vectors usually contain a promoter to direct polymerases to transcribe the heterologous coding region, a cloning site at which to introduce the heterologous coding region, and usually polyadenylation signals. Expression vectors include but are not limited to plasmids, retroviral vectors, viral and synthetic vectors.

Transformed host cells as used herein refer to cells which have coding regions of the present invention stably integrated into their genome, or episomally present as replicating or nonreplicating entities in the form of linear nucleic acid or transcript or circular plasmid or vector. Transformation or transformed as used herein refers to heterologous gene expression including but not limited to transient or stable transfection systems.

Direct administration as used herein refers to the direct administration of nucleic acid constructs which encode embodiments (e.g., SEQ ID NO:3, dominant/negative mutant version, antisense molecule, antibody molecule, modulator compound molecule) of the present invention or fragments thereof; and the direct administration of embodiments of the present invention or fragments thereof, and the in vivo introduction of molecules of the present invention preferably via an effective eukaryotic expression vector in a suitable pharmaceutical carrier. Polynucleotides and therapeutic molecules of the present invention may also be delivered in the form of nucleic acid transcripts.

ubiquitin-dependent proteolysis

Ubiquitination has recently become a focal point in cell biology as it is acknowledged in joining phosphorylation as a major protein modification device in regulation of cell physiology. The importance of ubiquitin-dependent proteolysis for selective elimination of biomolecules is indisputable for the maintenance of cellular integrity and physiology of the organism. The depth of current knowledge about the molecular mechanisms regulating ubiquitin-dependent proteolysis, combined with the understanding of how impairment of such processes, underlies pathological conditions, has opened the way for a mechanism-based approach for the development of new drugs. Rolfe, M., et al., *The Ubiquitin-Mediated Proteolytic Pathway as a Therapeutic Area*, J. Mol. Med. 75:5–17 (1997).

A growing number of cellular regulatory mechanisms are being linked to ubiquitin. For instance, ubiquitination is a widely utilized ligand-mediated means of modulating transmembrane receptor function. Mammalian transmembrane receptors found to undergo ligand-mediated ubiquitination are coupled to, or are themselves, tyrosine kinases. Ubiquitination of the T-cell receptor (TCR) is stimulated by antigen (MHC and peptide), superantigens, lectins that bind the TCR, or by anti-receptor antibodies. Moreover, correlations between dysregulated ubiquitination/proteasomal degradation and cellular transformation are striking. Weissman, A. M., *Regulating Protein Degradation by Ubiquitination, Review Immunology Today*, 18(4):189 (1997).

Ubiquitination is now implicated in regulating numerous cellular processes including: signal transduction, cell-cycle progression, receptor-mediated endocytosis, transcription (including activation-induced transcription in lymphocytes), organelle biogenesis and spermatogenesis. Abnormal accumulations of ubiquitinated species are found in intracellular inclusions in neuropathological conditions including Alzheimer's and Pick's diseases. The importance of regulated ubiquitination is demonstrated by the resistance of oncogenic counterparts of normal cellular ubiquitination substrates to this post-translational modification, and by correlations between malignant transformation and loss of function, or dysregulated function, of enzymes involved in ubiquitination. Proteasomes have recently been implicated in programmed cell death in neurons and thymocytes at points proximinal to activation of the interleukin-1β-converting enzyme (ICE) family of proteases. Morover, dysregulated ubiquitination contributes to malignant transformation, for example, oncogenic counterparts of normally ubiquitinated proteins are resistant to ubiquitination. Weissman, A. M., *Regulating Protein Degradation by Ubiquitination, Review Immunology Today*, 18(4): 189 (1997); Papavassiliou, A. G., et al., Science, 258:1941 (1992); Treier, M., et al., Cell, 78:787 (1994); Papa, F. R., et al., Nature, 366:319 (1993); Grimm, L. M., et al., EMBO, 15:3835 (1996); Sadoul, R., et al., EMBO, 15:3845 (1996).

E3 ligase

Ubiquitin-dependent proteolysis needs to be very selective in order to effectively regulate intracellular physiology. The component of the ubiquitin conjugation system generally believed to be the most directly involved in substrate recognition is the E3 protein ligase. See, e.g., Hochstrasser, M., *Ubiquitin-Dependent Protein Degradation*, Annu. Rev. Genet., 30:405 (1996). The first E3 ligase to be identified, E6-AP, is the best previously characterized member of the Hect-domain class. E6-AP was originally identified through its interaction with the E6 oncoprotein of the cancer-associated human papillomavirus types 16 and 18. The E6/E6-AP complex specifically binds to the tumor suppressor protein p53 and induces its ubiquitination and subsequent degradation. The cysteine residue necessary for thioester formation of E6-AP with ubiquitin is conserved among all of the Hect-domain class proteins. Because of this similarity these proteins have been termed Hect proteins, for 'Homologous to E6-AP C Terminus' (HECT).

An essential intermediate step in E6-AP-dependent protein ubiquitination is the formation of a thioester complex between ubiquitin and E6-AP. Furthermore, the direction of ubiquitin transfer is from E1 to E2 and then from E2 to E6-AP. This suggests that in this particular system, the E3 catalyzes the final attachment of ubiquitin to a substrate protein, rather than the E2 as shown for few other systems. The cysteine residue of E6-AP involved in thioester formation has been mapped to the carboxyl terminus. The carboxyl-terminal regions of several proteins from different organisms show significant similarity to the carboxyl terminus of E6-AP.

Furthermore, another ubiquitin protein ligase (E3) has been characterized as the neuronal precursor cell-expressed developmentally downregulated 4 (Nedd4). The biological structure is a multimodular protein composed of a C2 domain, 3 (or 4) WW domains, and a C-terminal ubiquitin protein ligase Hect domain. Nedd4 is a protein that interacts with the epithelial Na+ channel (ENaC) which is mediated by an association of the WW domains of Nedd4 with the proline-rich PY motifs (XPPXY, where X=any amino acid) of the ENaC subunits. Deletion or mutations within the PY motifs of the ENaC subunits have been genetically linked to Liddle syndrome, a hereditary form of systemic renal hypertension caused by an abnormal increase in ENaC activity. Recent work has described interaction of Nedd4 and Nedd4-like proteins with other PY motif-containing proteins, also mediated by the WW domains wherein the substrate specificity is determined by the E3 ligase. Staub, O., et al., EMBO, 15:2371 (1996).

human E3 ubiquitin protein ligase

The human E3 ligase described herein is a member of the Hect-domain containing ubiquitin-protein ligases, named for the highly conserved C-terminal portion of the molecule. SEQ ID NO:1 is a 5359 base cDNA nucleic acid sequence which encodes the novel human E3 ubiquitin protein ligase described herein (FIG. 1). SEQ ID NO:2 is a 2559 base translated structural coding region of the cDNA nucleic acid sequence which encodes the novel human E3 ubiquitin protein ligase (human homolog of the murine 'itchy' locus; Perry, W. L., et al., Nature Genetics, 18:143 (1998)). SEQ ID NO:3 is a 852 amino acid residue sequence of the human E3 ubiquitin protein ligase homolog described herein. SEQ ID NO:4, for comparison, is the 854 amino acid residue sequence of the murine E3 ubiquitin protein ligase mapped to 'itchy' locus as described by Perry, W. L., et al., Nature Genetics, 18:143 (1998); Hustad, C. M., et al., Genetics, 140:255 (1995).

A comparison alignment between the amino acid residue sequence of the novel human E3 ubiquitin protein ligase homolog described herein (SEQ ID NO:3), and the amino acid residue sequences of the murine E3 ubiquitin protein ligase (SEQ ID NO:4) is shown in FIG. 5. The native human protein (SEQ ID NO:3) is 96% homologous to the murine 'itchy' E3 ubiquitin ligase (SEQ ID NO:4), at the amino acid level. The Hect class of E3 ligases contain 3 or 4 protein-protein interaction domains known as WW domains, named for two conserved tryptophan (W) residues. Sequence alignment and structural features of the human E3 ligase protein (SEQ ID NO:3) compared to the mouse 'itchy' protein (SEQ ID NO:4) demonstrates that both proteins share the approximately 350 AA HECT domain at the C terminus; and both molecules have 4 WW protein interaction domains. Particularly pertaining to the human E3 ubiquitin protein ligase→WWI: positions 275–306 of SEQ ID NO:3; WWII: positions 307–340 of SEQ ID NO:3; WWIII: positions 386–420 of SEQ ID NO:3; WWIV: positions 427–460 of SEQ ID NO:3. Furthermore, the conserved cysteine residue where a ubiquitin linkage is expected to occur is also apparent at position 820 of SEQ ID NO:3. This residue position is of particular significance especially for the construction of pharmacologically valuable dominant negative mutants. The novel human E3 recombinant enzyme described herein, e.g., SEQ ID NO:3, is expected to have inherently high native catalytic activity. Moreover, any change (e.g., substitution or deletion) to the residue where ubiquitin linkage is expected to occur (SEQ ID NO:3, cysteine position 820) is expected to be significantly compromise the catalytic activity of the native human E3 ubiquitin protein ligase.

substrate

The novel human E3 ubiquitin protein ligase (e.g., SEQ ID NO:3) ubiquitinates specific intracellular biological molecules in vivo to effect selective destruction and swift regulation of cellular physiology. Biological activity refers to the ability of the novel human E3 ubiquitin protein ligase and variations thereof contemplated herein to bind ubiquitin and/or transfer ubiquitin to a substrate under biological conditions. Substrates include the likes of intracellular messenger biological molecules, receptors, ligands, signal transduction molecules, transcriptional activators, cytokines, kinases, phosphatases and phosphorylases, especially which mediate physiological conditions such as inflammation, autoimmune disease, neurological disease, apoptosis, endothelial cell physiology (e.g., proliferation, differentiation), peripheral vascular disease, angiogenesis, cancer, anemia, hematopoietic disorders, cachexia, leukemia, pulmonary disorders, arthritis, diabetes, and viral infection. Pharmacological activity, as used herein in reference to the novel human E3 ubiquitin protein ligase (e.g., SEQ ID NO:3) and variations thereof contemplated herein, refers to the ability to modulate protein degradation or selective proteolysis and/or otherwise modulate physiological conditions associated with aberrant ubiquitin dependent proteolysis in human physiology (e.g., disorders manifested by aberrant forms and/or abnormal levels of the native E3 ubiquitin protein ligase).

pharmacological significance

The control of hematopoiesis is a highly regulated process that responds to a number of physiological stimuli in the human body. Differentiation, proliferation, growth arrest, or apoptosis of blood cells depends on the presence of appropriate cytokines and their receptors, as well as the corresponding cellular signal transduction cascades. Hu, Mickey C. -T., et al., Genes & Development, 10:2251(1996). Generation of mature leukocytes, for instance, is a highly regulated process which responds to various environmental and physiological stimuli. Cytokines cause cell proliferation, differentiation or elimination, each of these processes being dependent on the presence of appropriate cytokine receptors and the corresponding signal transduction elements. Moreover, the stimulation of quiescent B- and T-lymphocytes occur via antigen receptors which exhibit remarkable homology to cytokine receptors. Grunicke, Hans H., *Signal Transduction Mechanisms in Cancer*, Springer-Verlag (1995). See also, Suchard, S. J., et al., *Mitogen-Activated Protein Kinase Activation During IgG-Dependent Phagocytosis in Human Neutrophils*, J. Immunol., 158:4961 (1997).

The identification of a single gene underlying an inflammatory syndrome provides significant potential to identify novel targets for anti-inflammatory drugs, inter alia. Modulators of the human E3 ubiquitin protein ligase described herein accordingly have significant potential as novel anti-inflammatory agents as well as agents to promote wound-healing. See, D'Andrea, A. D., et al., Nature Genetics, 18:97 (1998). Moreover, compounds which modulate the biological activity of the human E3 ubiquitin protein ligase in vivo are expected to to influence hematopoiesis. The 'itchy' knockout mice (murine E3 ubiquitin protein ligase (SEQ ID NO:4)) have demonstrated enhanced hematopoiesis, manifested, for example, by accelerated development of the erythroid, myeloid, and lymphoid lineages. The homozygous mouse has been demonstrated to exhibit an apparent pan-hematopoiesis, resulting in the accumulation of inflammatory cells in organs and the skin and a macrophage infiltrate in the lung. The murine E3 ligase (SEQ ID NO:4), involved in ubiquitin-mediated protein degradation, is believed to specifically mediate the turnover of growth factor signal transduction proteins in the hematopoietic lineages. By analogy, the human homolog E3 ubiquitin protein ligase described herein (SEQ ID NO:3) is expected to likewise significantly influence hematopoiesis. Moreover, results indicate that ubiquitin-dependent proteolysis is an important mediator of the immune response in vivo and provides evidence for the 'itchy' E3's role in inflammation and the regulation of epithelial and haematopoietic cell growth. Perry, W. L., et al., Nature Genet., 18:143 (1998); Rolfe, M., et al., *The Ubiquitin-Mediated Proteolytic Pathway as a Therapeutic Area*, J. Mol. Med. 75:5–17 (1997). Accordingly, specific modulation of the biological and/or pharmacological activity of the human "itchy" E3 ligase, e.g., SEQ ID NO:3, via administration of a compound modulator or heterologous expression or administration of a dominant negative mutant version is expected to significantly influence inflammation as well as hematopoiesis. Example human E3 ubiquitin protein ligase substrates include, but are not limited to, GM-CSF and its receptor, G-CSF and its receptor, SCF and its receptor c-kit, IL-3 and IL-3r, IL-5 and IL-5r, and IL-6 and IL-6r.

Hematopoiesis can be severely compromised by cytotoxic chemotherapy and irradiation. High-dose conditioning therapies that include total body irradiation, for instance, are notably myelotoxic and require the transplantation of hematopoietic progenitor cells. See, e.g., Thomas, E. D., et al., N. Engl. J. Med., 25:491 (1987); Berenson, R. J. et al., Blood. 77:1717 (1991). Such adoptive cellular immunotherapy is regularly accompanied by growth factor administration, e.g., erythropoietin (Epogen), G-CSF (Neupogen), GM-CSF, and thrombopoietin in respective therapeutic applications. Modulators of the novel human E3 ubiquitin protein ligase as described herein are therefore contemplated as therapeutic agents to compete with the likes of erythropoietin (Epogen), G-CSF (Neupogen), and thrombopoietin in the respective applications. Applications are also contemplated for supportive hematopoietic care, including cancer therapies that impair bone marrow function and AIDS.

Cachexia is a condition characterized by severe muscle atrophy, weight loss and emaciation. Ubiquitin dependent proteolysis has been linked to the skeletal muscle loss during cachexia as well in in tumors. Medina, R., et al., Biomed. Biochim. Acta. 50:4 (1991); Temparis, S., et al., Cancer Research, 54: 5568 (1994); Tiao, G. et al., J. Clin. Invest., 94:2255 (1994). Furthermore, ubiquitin dependent proteolysis has recently been implicated in the down regulation of signal transducing receptors. Particularly the involvement of the ubiquitin conjugation system in the ligand induced endocytosis and degradation of the growth hormone receptor may be of particular importance in cachexia conditions. The b2-Adrenergic Agonist, Clenbuterol, for instance, has been demonstrated to prevent enhanced muscle protein degradation, and that normalization of protein breakdown is achieved through a decrease of the hyperactivation of the ubiquitin dependent proteolysis system. Costelli, P., et al., J. Clin. Invest 95:2367 (1995).

The novel human E3 recombinant enzyme described herein, e.g., SEQ ID NO:3, is expected to have inherently high native catalytic activity. Clearly defined biological activity permits easy adaptation of the ligase to methods for identifying compounds that modulate the biological and/or pharmacological activity of the novel human E3 ubiquitin protein ligase and variations thereof contemplated herein, for instance, via automated high throughput biochemical assays, e.g., scintillation proximity assays, further described infra. For instance, a specific low molecular weight inhibitor of ubiquitin transfer onto cyclin B, targeting the E3 involved in this process, would prevent cyclin B destruction and would be expected to be a very strong cytostatic agent. Rolfe, M., et al., *The Ubiquitin-Mediated Proteolytic Pathway as a Therapeutic Area*, J. Mol. Med. 75:5–17 (1997). Accordingly, specific modulation of the biological and/or pharmacological activity of the novel human E3 ubiquitin protein ligase, e.g., SEQ ID NO:3, via administration of a compound modulator or heterologous expression or administration of a dominant negative mutant version is expected to have a high degree of biological specificity for the treatment of physiological conditions including, but not limited to, inflammation, autoimmune disease, neurological disease, apoptosis, endothelial cell physiology (e.g., proliferation, differentiation), peripheral vascular disease, angiogenesis, cancer, anemia, hematopoietic disorders, cachexia, leukemia, pulmonary disorders, arthritis, diabetes, and viral infection.

variants

The present invention also encompasses variants of the human E3 ubiquitin protein ligase SEQ ID NO:3. A variant substantially as depicted in SEQ ID NO:3, for instance, is one having 98% total amino acid sequence similarity to the human E3 ubiquitin protein ligase amino acid sequence (SEQ ID NO:3) or a biologically active fragment thereof. A preferred variant substantially as depicted in SEQ ID NO:3 is one which retains at least one of the amino acid residues which are characteristic of the human homolog E3 ubiquitin protein ligase described herein.

A "variant" of the human E3 ubiquitin protein ligase molecule of the present invention may have an amino acid sequence that is different by one or more amine acid "substitutions". The variant may have "conservative" changes, wherein a substituted amine acid has similar structural or chemical properties, eg, replacement of leucine with isoleucine. More rarely, a variant may have "nonconservative" changes, eg, replacement of a glycine with a tryptophan. Similar minor variations may also include amine acid deletions or insertions, or both. Guidance in determining which and how many amine acid residues may be substituted, inserted or deleted without abolishing biological or immunological activity, for instance, may be found using computer programs well known in the art, for example, DNAStar software.

The present invention relates to nucleic acid (SEQ ID NO:1 and SEQ ID NO:2) and amino acid sequences (SEQ ID NO:3) of the novel human E3 ubiquitin protein ligase and variations thereof and to the use of these sequences to identify compounds that modulate the activity of E3 ubiquitin protein ligase under biological conditions as well as human physiology.

The invention further relates to the use of the nucleic acid sequences described herein in expression systems as assays for agonists or antagonists of the E3 ubiquitin protein ligase.

The invention also relates to the diagnosis, study, prevention, and treatment of disease related to the human E3 ubiquitin protein ligase and/or diseases mediated by the biomolecule.

Polynucleotide sequences which encode the human E3 ubiquitin protein ligase(SEQ ID NO:3) or a functionally equivalent derivative thereof may be used in accordance with the present invention which comprise deletions, insertions and/or substitutions of the SEQ ID NO:2 nucleic acid sequence. Biologically active variants of the biomolecule of the present invention may also be comprised of deletions, insertions or substitutions of SEQ ID NO:3 amino acid residues. A purified polynucleotide comprising a nucleic acid sequence encoding the polypeptide having the sequence substantially as depicted in SEQ ID NO:3 or a biologically active fragment thereof is a particularly preferred embodiment of the present invention.

Amino acid substitutions of SEQ ID NO:3 may be made, for instance, on the basis of similarity in polarity, charge, solubility, hydrophobicity, hydrophilicity, and/or the amphipathic nature of the residues as long as the pharmacological or biological activity of the E3 ubiquitin protein ligase is retained.

Dominant/negative mutants are also contemplated wherein codons for one or more known functional residues are deleted or changed in the coding region (e.g., SEQ ID NO:2) in order to encode a mutant variation having valuable pharmacological function. For example, characteristic residues for ubiquitin transfer (e.g., the conserved cysteine residue at SEQ ID NO:3 position 820 where a ubiquitin linkage is expected to occur) may be changed or deleted. Methods of treatment of conditions manifested by aberrant forms and/or abnormal levels of the native E3 ubiquitin protein ligase via administration of a polypeptide substantially as depicted in SEQ ID NO:3 or a pharmacologically active fragment thereof, or a nucleic acid substantially as depicted in SEQ ID NO:1, as referred to herein, is defined to encompass dominant/negative mutant versions of these entities.

For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine phenylalanine, and tyrosine.

Nucleic acid sequences which encode the amino acid sequence of the human ubiquitin ligase described herein are of an exponential sum due to the potential substitution of degenerate codons (different codons which encode the same amino acid). The oligonucleotide sequence selected for heterologous expression is therefore preferably tailored to meet the most common characteristic tRNA codon recognition of the particular host expression system used as well known by those skilled in the art.

Suitable conservative substitutions of amino acids are known to those of skill in this art and may be made without altering the biological activity of the resulting polypeptide, regardless of the chosen method of synthesis. The phrase "conservative substitution" includes the use of a chemically derivatized residue in place of a non-derivatized residue provided that such polypeptide displays the desired binding activity. D-isomers as well as other known derivatives may also be substituted for the naturally occurring amino acids. See, e.g., U.S. Pat. No. 5,652,369, *Amino Acid Derivatives*, issued Jul. 29, 1997. Substitutions are preferably, although not exclusively, made in accordance with those set forth in TABLE 1 as follows:

TABLE 1

| Original residue | Conservative substitution |
| --- | --- |
| Ala (A) | Gly; Ser; Val; Leu; Ile; Pro |
| Arg (R) | Lys; His; Gln; Asn |
| Asn (N) | Gln; His; Lys; Arg |
| Asp (D) | Glu |
| Cys (C) | Ser |
| Gln (Q) | Asn |
| Glu (E) | Asp |
| Gly (G) | Ala; Pro |
| His (H) | Asn; Gln; Arg; Lys |
| Ile (I) | Leu; Val; Met; Ala; Phe |
| Leu (L) | Ile; Val; Met; Ala; Phe |
| Lys (K) | Arg; Gln; His; Asn |
| Met (M) | Leu; Tyr; Ile; Phe |
| Phe (F) | Met; Leu; Tyr; Val; Ile; Ala |
| Pro (P) | Ala; Gly |
| Ser (S) | Thr |
| Thr (T) | Ser |
| Trp (W) | Tyr; Phe |
| Tyr (Y) | Trp; Phe; Thr; Ser |
| Val (V) | Ile; Leu; Met; Phe; Ala |

The nucleotide sequences of the present invention may also be engineered in order to alter a coding sequence for a variety of reasons, including but not limited to, alterations which modify the cloning, processing and/or expression of the gene product. For example, mutations may be introduced using techniques which are well known in the art, eg, site-directed mutagenesis to insert new restriction sites, to alter glycosylation patterns, to change codon preference, etc.

Included within the scope of the present invention are alleles of the human E3 ubiquitin protein ligase molecule of the present invention. As used herein, an "allele" or "allelic sequence" is an alternative form of the E3 ubiquitin protein ligase molecule described herein. Alleles result from nucleic acid mutations and mRNA splice-variants which produce polypeptides whose structure or function may or may not be altered. Any given gene may have none, one or many allelic forms. Common mutational changes which give rise to alleles are generally ascribed to natural deletions, additions or substitutions of amino acids. Each of these types of changes may occur alone, or in combination with the others, one or more times in a given sequence.

The present invention relates, in part, to the inclusion of the polynucleotide encoding the novel E3 ubiquitin protein ligase molecule in an expression vector which can be used to transform host cells or organisms. Such transgenic hosts are useful for the production of the novel selective degradation molecule and variations thereof described herein.

The nucleic acid sequence also provides for the design of antisense molecules useful in downregulating, diminishing, or eliminating expression of the genomic nucleotide sequence in cells including but not limited to hematopoietic, endothelial, and tumor or cancer cells.

The human E3 ubiquitin protein ligase biomolecule of the present invention can also be used in screening assays to identify blockers, antagonists or inhibitors which bind, emulate substrate, or otherwise inactivate or compete with the biomolecule. The novel E3 ubiquitin protein ligase can also be used in screening assays to identify agonists which activate the E3 ubiquitin ligase or otherwise induce the production of or prolong the lifespan of the biomolecule in vivo or in vitro.

The invention also relates to pharmaceutical compounds and compositions comprising the human E3 ubiquitin protein ligase molecule substantially as depicted in SEQ ID NO:3, or fragments thereof, antisense molecules capable of disrupting expression of the naturally occurring gene, and agonists, antibodies, antagonists or inhibitors of the native biomolecule.

FIG. 7 displays PCR primers, SEQ ID NO:5 and SEQ ID NO:6, which are used to amplify the 2559 bp coding region (SEQ ID NO:2) of the novel human E3 ubiquitin protein ligase from human tissue.

generally acceptable vectors

In accordance with the present invention, polynucleotide sequences which encode the human E3 ubiquitin protein ligase polypeptide, fragments of the polypeptide, fusion proteins, or functional equivalents thereof may be used in recombinant DNA molecules that direct the expression of the ubiquitin ligase biomolecule in appropriate host cells. Due to the inherent degeneracy of the genetic code, other DNA sequences which encode substantially the same or a functionally equivalent amino acid sequence, may be used to clone and express the human biomolecule as well as variations thereof contemplated herein. As will be understood by those of skill in the art, it may be advantageous to produce the human E3 ubiquitin ligase encoding nucleotide sequences which possess non-naturally occurring codons.

Specific initiation signals may also be required for efficient translation of an E3 ubiquitin ligase nucleic acid sequence. These signals include the ATG initiation codon and adjacent sequences. In cases where the human E3 ubiquitin ligase nucleic acid sequence, e.g., SEQ ID NO:2, its initiation codon and upstream sequences are inserted into the appropriate expression vector, no additional translational control signals may be needed. However, in cases where only coding sequence, or a portion thereof, is inserted, exogenous transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic.

Nucleic acid sequences, e.g., SEQ ID NO:2, may be recombinantly expressed to produce a pharmacologically active E3 ubiquitin ligase biomolecule by molecular cloning into an expression vector containing a suitable promoter and other appropriate transcription regulatory elements, and transferred into prokaryotic or eukaryotic host cells to produce the novel polypeptide. Techniques for such manipulations are, for instance, fully described in Sambrook, J., et al., Molecular Cloning Second Edition, Cold Spring Harbor Press (1990), and are well known in the art.

Expression vectors are described herein as DNA sequences for the transcription of cloned copies of genes and the translation of their mRNAs in an appropriate host cell. Such vectors can be used to express nucleic acid sequences in a variety of hosts such as bacteria, bluegreen algae, plant cells, insect cells, fungal cells, human, and animal cells. Specifically designed vectors allow the shuttling of DNA between hosts such as bacteria-yeast, or bacteria-animal cells, or bacteria-fungal cells, or bacteria-invertebrate cells.

A variety of mammalian expression vectors may be used to express the recombinant E3 ubiquitin ligase molecule and variations thereof disclosed herein in mammalian cells. Commercially available mammalian expression vectors which are suitable for recombinant expression, include but are not limited to, pcDNA3 (Invitrogen), pMC1neo (Stratagene), pXT1 (Stratagene), pSG5 (Stratagene), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and 1ZD35 (ATCC 37565), pLXIN and pSIR (CLONTECH), pIRES-EGFP (CLONTECH). INVITROGEN corporation provides a wide variety of commercially available mammalian expression vector/systems which can be effectively used with the present invention. INVITROGEN, Carlsbad, Calif. See, also, PHARMINGEN products, vectors and systems, San Diego, Calif.

Baculoviral expression systems may also be used with the present invention to produce high yields of biologically active protein. Vectors such as the CLONETECH, BacPak™ Baculovirus expression system and protocols are preferred which are commercially available. CLONTECH, Palo Alto, Calif. Miller, L. K., et al., Curr. Op. Genet. Dev. 3:97 (1993); O'Reilly, D. R., et al., Baculovirus Expression Vectors. A Laboratory Manual, 127. Vectors such as the INVITROGEN, MaxBac™ Baculovirus expression system, insect cells, and protocols are also preferred which are commercially available. INVITROGEN, Carlsbad, Calif. example host cells Host cells transformed with a nucleotide sequence which encodes a E3 ubiquitin ligase molecule of the present invention may be cultured under conditions suitable for the expression and recovery of the encoded protein from cell culture. Particularly preferred embodiments of the present invention are host cells transformed with a purified polynucleotide comprising a nucleic acid sequence encoding the polypeptide having the sequence substantially as depicted in SEQ ID NO:3 or a biologically active fragment thereof. Cells of this type or preparations made from them may be used to screen for pharmacologically active modulators of the activity of the human E3 ubiquitin ligase. Modulators thus identified will be used for the treatment of disorders manifested by aberrant forms and/or abnormal levels of the native E3 ubiquitin protein ligase.

Eukaryotic recombinant host cells are especially preferred as otherwise descibed herein or are well known to those skilled in the art. Examples include but are not limited to yeast, mammalian cells including but not limited to cell lines of human, bovine, porcine, monkey and rodent origin, and insect cells including but not limited to Drosophila and silkworm derived cell lines. Cell lines derived from mammalian species which may be suitable and which are commercially available, include but are not limited to, L cells L-M(TK-) (ATCC CCL 1.3), L cells L-M (ATCC CCL 1.2), 293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26) and MRC-5 (ATCC CCL 171).

The expression vector may be introduced into host cells expressing the ubiquitin ligase polypeptide via any one of a number of techniques including but not limited to transformation, transfection, lipofection, protoplast fusion, and electroporation. Commercially available kits applicable for use with the present invention for hererologous expression, including well-characterized vectors, transfection reagents and conditions, and cell culture materials are well-established and readily available. CLONTECH, Palo Alto, Calif.; INVITROGEN, Carlsbad, Calif.; PHARMINGEN, San Diego, Calif.; STRATAGENE, LaJolla, Calif. The expression vector-containing cells are clonally propagated and individually analyzed to determine the level of the novel E3 ubiquitin protein ligase production. Identification of host cell clones which express the polypeptide may be performed by several means, including but not limited to immunological reactivity with antibodies described herein, and/or the presence of host cell-associated specific E3 ubiquitin protein ligase activity, and/or the ability to covalently cross-link specific substrate to the E3 ubiquitin protein ligase polypeptide with the bifunctional cross-linking reagent disuccinimidyl suberate or similar cross-linking reagents.

The ubiquitin protein ligase biomolecule of the present invention may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals (Porath, J., Protein Exp. Purif., 3:263 (1992)), protein A domains that allow purification on immobilized immunoglobulin, and the domain utilized in the FLAGS extension/affinity purification system (Immunex Corp, Seattle Wash.). The inclusion of a cleavable linker sequences such as Factor XA or enterokinase (Invitrogen, San Diego Calif.) between the purification domain and the ubiquitin protein ligase coding region is useful to facilitate purification.

Systems such as the CLONTECH, TALON™ nondenaturing protein purification kit for purifying 6xHis-tagged proteins under native conditions and protocols are preferred which are commercially available. CLONTECH, Palo Alto, Calif.

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation and acylation. Post-translational processing which cleaves a nascent form of the protein may also be important for correct insertion, folding and/or function. Different host cells such as CHO, HeLa, MDCK, 293, WI38, NIH-3T3, HEK293 etc., have specific cellular machinery and characteristic mechanisms for such post-translational activities and may be chosen to ensure the correct modification and processing of the introduced, foreign protein.

For long-term, high-yield production of the recombinant molecule, stable expression is preferred. For example, cell lines which stably express the novel E3 ubiquitin protein ligase polypeptide may be transformed using expression vectors which contain viral origins of replication or endogenous expression elements and a selectable marker gene. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clumps of stably transformed cells can be proliferated using tissue culture techniques appropriate to the cell type.

The human E3 ubiquitin protein ligase and variations thereof described herein can be produced in the yeast S. cerevisiae following the insertion of the optimal cDNA cistron into expression vectors designed to direct the intracellular or extracellular expression of the heterologous protein. In the case of intracellular expression, vectors such as EmBLyex4 or the like are ligated to the beta subunit cistron. See, e.g., Rinas, U., et al., Biotechnology, 8:543 (1990); Horowitz, B., et al., J. Biol. Chem., 265:4189 (1989). For extracellular expression, a ubiquitin protein ligase coding region, e.g., SEQ ID NO:2, is ligated into yeast expression vectors which may employ any of a series of well-characterized secretion signals. Levels of the expressed ubiquitin ligase molecule may be determined, for example, by means of the assays described herein.

A variety of protocols for detecting and measuring the expression of the human E3 ubiquitin protein ligase, using either polyclonal or monoclonal antibodies specific for the protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes may be employed. Well known competitive binding techniques may also be employed. See, e.g., Hampton, R., et al. (1990), *Serological Methods—a Laboratory Manual*, APS Press, St Paul Minn.; Maddox, D. E., et al., J. Exp. Med. 158:1211.

example transformations

E coli transformations are generally carried out via electroporation. 400 ml cultures of strains DH5a or BL21 (DE3) are grown in L-broth to an OD 600 of 0.5 and harvested at 2,000 g. The cells are washed twice in ice-cold deionised water, resuspended in 1 ml 10% glycerol and stored in aliquots at −70° C. Ligation mixes are desalted using millipore V series membranes (0.0025 mm pore). 40 ml of cells are incubated with 1 ul of ligation mix or plasmid DNA on ice for 10 minutes in 0.2 cm electroporation cuvettes, then pulsed using a Gene Pulser apperatus (BioRad) at ^0.5 kVcm$^{-1}$, 25 mF, 250½. Transformants are selected on L-agar supplemented with tertracyline at 10 mg/ml or ampicillian at 100 mg/ml.

example expression/purification

The novel human E3 ubiquitin protein ligase, e.g., SEQ ID NO:2, is expressed from a pET vector (e.g., 14b–16b or 28a–c(+) (NOVAGEN)) in BL21 cells, in such a way to produce a recombinant protein containing a 6-histidine tag immediately adjacent to the N-terminal methionine. The 6-His tag is used to aid purification of the recombinant protein as is passed through a nickel chelating column (NOVAGEN).

over-expression of the ubiquitin ligase in cell-lines

Transient and/or stable eucaryotic transfectant cells comprised of the coding region(s) described herein are contemplated for high-level expression of the novel human E3 ubiquitin protein ligase as well as variations thereof.

Eucaryotic transfectants are preferred embodiments of the present invention for employment in studies for the identification molecules which modulate the human E3 ubiquitin protein ligase described herein in vivo. HEK cells, for example, may be employed.

Transient expression of coding regions for the human E3 ubiquitin protein ligase polypeptide can be achieved by straight transfection into mammalian cells, by standard techniques. Omari, K. et al., J. Physiol., 499:369, (1997); Panyi, G. et al., J. Gen. Physiol., 107(3):409 (1996). High level transient expression may be achieved using standard viral systems, e.g., Baculovirus, Adenovirus, or Vaccinia virus. Functionally expressed representatives resulting from these systems are typically 5–500 K per cell. Kamb, A., Methods Enzymol. 207:423 (1992); Sun, T. et al., Biochemistry, 33(33):9992 (1994); Spencer, R. H., et al., J. Biol. Chem., 272:2389 (1997).

Stable transfection of heterologous cells using sequences which encode the novel E3 ubiquitin protein ligase described herein (SEQ ID NO:3) or pharmacologically active variations or fragments thereof can be generated using, for example, NIH-3t3, L929, COS, HEK, or CHO cells. See, e.g., EMBO, 11(6):2033 (1992); Grissmer, et al., Mol. Pharm., 45:1227 (1994).

A preferred vector for use with the present invention is pcDNA/Neo, which is commercially available from INVITROGEN, Carlsbad, Calif.

Cells, NIH-3t3, for example, are grown to 50% confluency in 60 mm plates (media and conditions are according to requirements of the particular cell line) and transfected with 5 ug of pure DNA comprising a coding region for the human E3 ubiquitin protein ligase, e.g. SEQ ID NO:2, in pcDNA/Neo using the Lipofection reagent, as described by the supplier (LIFE TECHNOLOGIES Gibco BRL, Bethesda, Md.). After transfection, the cells are incubated at 37° C., conditions for 3 days in medium with 10% FCS. Cells are trypsinized seeded onto 100 mm dishes, and then selected with 300 ug/ml of G418 (Neomycin). Only cells that have stable integration of the heterologous coding region will grow in the presence of G418, which is confered by the Neomycin-resistance gene in the plasmid. Isolated clones are processed for 2–3 rounds of purification.

E1

All ubiquitin-activating (E1) proteins and genes corresponding thereto are contemplated for use in biological assays as well as drug screen assays described herein. SEQ ID NO:10 (FIG. 12), for example, as an embodiment for use in the methods described and contemplated herein, is the 3177 base translated structural coding region of the nucleic acid sequence which encodes the previously described 1058 amino acid residue human E1 ubiquitin activating enzyme (Uba1). Ayusawa, D., et al., Cell Struct. Funct., 17:113 (1992). See, also, Jentsch, S., et al., *Genetic Analysis of the Ubiquitin System, Biochim. Biophys.* Acta, 1089:127 (1991); McGrath, J. P., et al., *UBA1—An Essential Yeast Gene Encoding Ubiquitin-Activating Enzyme*, EMBO 10: 227 (1991); *Immunofluorescent Localization of the Ubiquitin-Activating Enzyme, E1, to the Nucleus and Cytoskeleton*, Am. J. Physiol., 264:C9; Cook, J. C., et al., *Ubiquitin-Activating Enzyme in Cultured Cells*, PNAS, 92:3454 (1995); Nagai, Y., et al., *Ubiquitin-Activating Enzyme, E1, is Phosphorylated in Mammalian Cells by the Protein Kinase Cdc2*, J. Cell Sci., 108:2145 (1995).

E2

Similarly, all ubiquitin-conjugating enzymes (E2) proteins and genes corresponding thereto are contemplated for use in biological assays as well as drug screen assays described herein. SEQ ID NO:11 (FIG. 13), for example, as an embodiment for use in the methods described and contemplated herein, is the 444 base translated structural coding region of the nucleic acid sequence which encodes the previously described 147 amino acid residue E2 ubiquitin conjugating enzyme E217k (ub10a). Wing S. S., et al., Biochem. J., 305:125 (1995) [The E2 human version (Ubc2) is preferred as described by Koken, M., et al., PNAS, 88:8865 (1991)]. Other embodiments of E2 ubiquitin conjugating enzymes for use in methods of the present invention include, but are not limited to: Ubc2/Rad6 (Koken, M., et al., PNAS, 88:8865 (1991) *Human E2*), Ubc3/Cdc34 (Plon, et al., PNAS, 90:10484 (1993)), Ubc4/Ubc5B (Jensen, et al., J. Biol. Chem., 270:30408 (1995) & Rolfe, et al., PNAS, 92:3264 (1995)), Ubc5/Ubc5A (Jensen, et al., J. Biol. Chem., 270:30408 (1995) & Schneffer, et al., PNAS, 91:8797 (1994)), Ubc5C (Jensen, et al., J. Biol. Chem., 270:30408 (1995)), Ubc6 (Nuber, et al., J Biol Chem 271:2795 (1996)), Ubc7 (Nuber, et al., J Biol Chem 271:2795 (1996) & Robinson, et al., Mammal Genome, 6:725 (1995)), Ubc8 (Kaiser, et al., J Biol Chem, 269:8797 (1994)), Ubc9 (Kovalenko, et al., PNAS, 93:2958 (1996)), Watanabe, et al., Cytogen Cell Gen ., 72:86 (1996), Ubc-epi (Liu, et al., *cDNA Cloning of a Novel Human Ubiquitin Carrier Protein*, J. Biol. Chem., 267:15829(1992)), and Ubc-bendless: GENBANK Accession Number D83004. See, generally, Rolfe, et al., *The Ubiquitin-Mediated Proteolytic Pathway as a Therapeutic Area*, J. Mol. Med., 75:5 (1997)). See, also, Baboshina, O. V., et al., *Novel Multiu-* biquitin Chain Linkages Catalysed by the Conjugating Enzymes E2(EPF) and RAD6 are recognized by the 26-S Proteasome Subunit, J. Biol Chem., 271:2823 (1996); Dohmen, R. J., et al., The N-End Rule Is Mediated by the Ubc2(Rad6) Ubiquitin-Conjugating Enzyme, PNAS, 88:7351 (1991); Seufert, W., et al., Ubiquitin-Conjugating Enzymes Ubc4 and Ubc5 Mediate Selective Degradation of Short-Lived and Abnormal Proteins, EMBO, 9:543 (1990); Cook, W. J., et al., 3-Dimensional Structure of a Ubiquitin-Conjugating Enzyme (E2), J. Biol. Chem., 267:15116 (1992); Bartel, B., et al., The Recognition Component of the N-End Rule Pathway, EMBO, 9:3179 (1990).

ubiquitin

Ubiquitin is available, labeled and unlabeled, from a variety of well-known commercial suppliers. SEQ ID NO:7 is the 156 amino acid precursor peptide to the mature 76 amino acid residue sequence of human ubiquitin (FIG. 9) (Lund P. K., et al., J. Biol. Chem., 260:7609 (1985)). FIG. 10 displays SEQ ID NO:8 which is the mature 76 amino acid residue sequence of native human ubiquitin (positions 1–76 of SEQ ID NO:7). SEQ ID NO:9 (FIG. 11) is the 471 base translated structural coding region of the cDNA nucleic acid sequence which encodes the 156 amino acid precursor peptide (SEQ ID NO:7) to the mature 76 amino acid residue sequence of native human ubiquitin (positions 1–76 of SEQ ID NO:7) (Lund P. K., et al., J. Biol. Chem., 260:7609 (1985)). The human E3 ubiquitin protein ligase (SEQ ID NO:3) ubiquitinates specific intracellular biological molecules in vivo including the likes of intracellular messenger biological molecules, receptors, ligands, signal transduction molecules, transcriptional activators, cytokines, kinases, and phosphorylases, especially which mediate physiological conditions such as inflammation, autoimmune disease, neurological disease, apoptosis, endothelial cell physiology (e.g., proliferation, differentiation), peripheral vascular disease, angiogenesis, cancer, anemia, hematopoietic disorders, cachexia, leukemia, pulmonary disorders, arthritis, diabetes, and viral infection to effect selective destruction and swift regulation of cellular physiology. Any potential substrate may be used in biological assays as well as drug screen assays described herein including, but not limited to, substrates referred to in references cited herein or which are otherwise known or identified in the art of human pathophysiology.

general biological assays

Methods of identifying compounds that modulate the biological activity of a human E3 ubiquitin protein ligase, are contemplated and provided herein and in the EXAMPLES which comprise combining a candidate compound modulator of human E3 ubiquitin protein ligase biological activity with a human E3 ubiquitin protein ligase polypeptide having the sequence substantially as depicted in SEQ ID NO:3, and measuring an effect of the candidate compound modulator on the biological activity.

general pharmacological assays

The human E3 ubiquitin protein ligase described herein may be assayed for its ability to modulate protein degradation or selective proteolysis and/or otherwise modulate conditions associated with aberrant ubiquitin dependent proteolysis in intracellular physiology (disorders manifested by aberrant forms and/or abnormal levels of the native E3 ubiquitin protein ligase). Methods of identifying compounds that modulate the pharmacological activity of a human E3 ubiquitin protein ligase, comprise combining a candidate compound modulator of human E3 ubiquitin protein ligase pharmacological activity with a host-cell expressing a human E3 ubiquitin protein ligase polypeptide having the sequence substantially as depicted in SEQ ID NO:3, and measuring an effect of the candidate compound modulator on the pharmacological activity.

scintillation proximity assay

Scintillation Proximity Assay (SPA) technology is developed which allows the rapid and sensitive assay of a wide variety of molecular interactions in a homogeneous system. AMERSHAM, Bucks, UK. The decay of a radioactive atom releases sub-atomic particle radiation. The distance these particles travel through the medium in which they are released is dependent upon the energy of the particle. In the scintillation proximity assay scintillant is incorporated into small fluoromicrospheres. These microspheres or 'beads' are derivatized in such a way as to bind specific molecules. If a radioactive molecule is bound to the bead, the radiation is in close enough proximity to stimulate the scintillant in order to emit light (unbound isotopes are too distant). The technique of SPA simplifies the process of assay design by removing the necessity to separate bound from free ligand, allowing assays to be performed and counted in one tube or in 96-well microplates. Moreover, assay speed is increased, and the need for filters, solvents, vials and scintillation reagents is eliminated. SPA is employed in screening assays as diverse as protein:protein, protein:DNA and cell adhesion molecule interactions. SPA represents a major drug screening technology, which has already been used successfully to identify a large number of candidate therapeutic compounds against a multitude of targets. See, EXAMPLE III.

Figure 8:
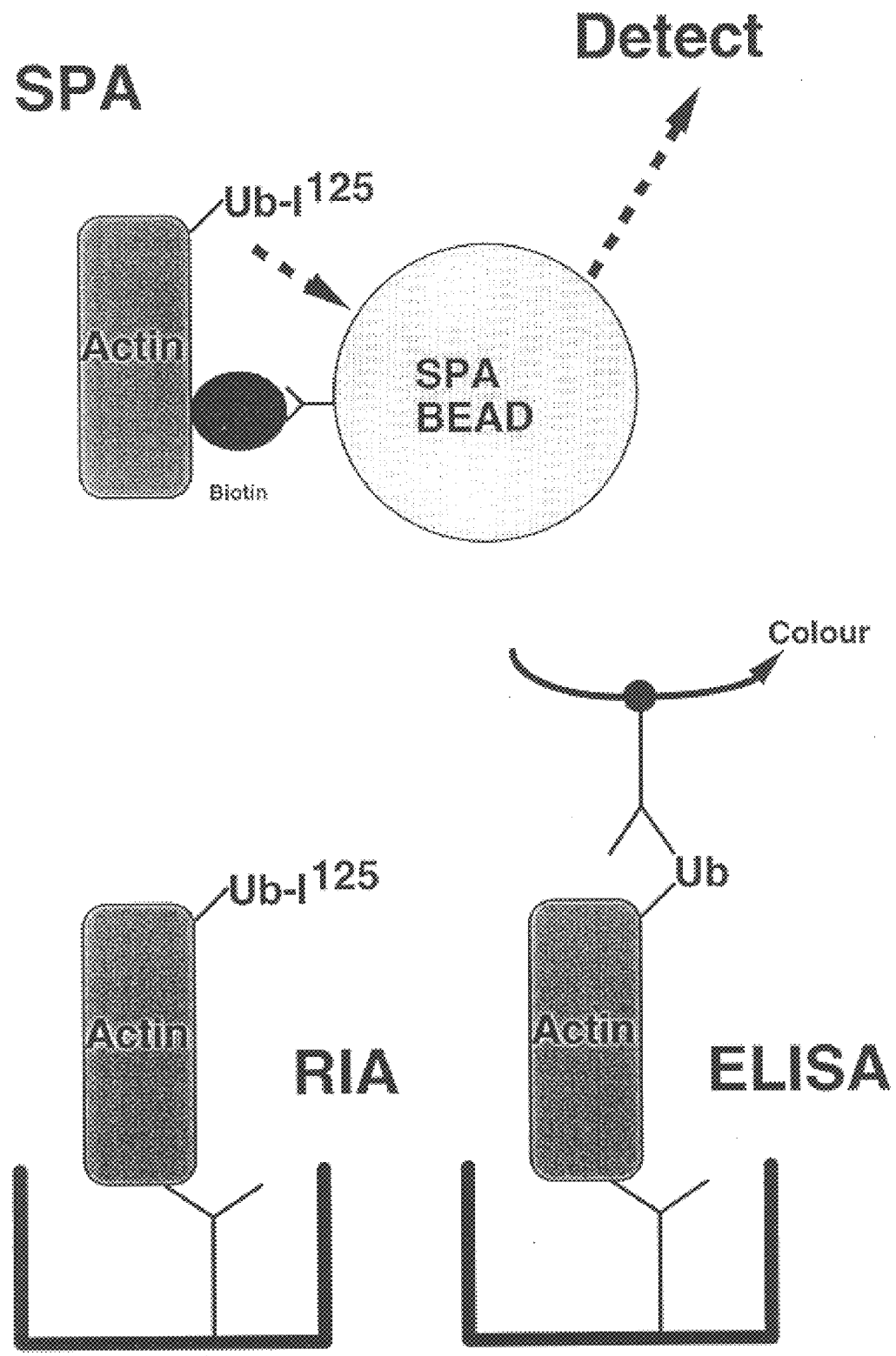
FIG. 8 shows a schematic representation of example Scintillation Proximity Assays (SPA), as well as RIA and ELISA Assays.

FIG. 8 shows a schematic representation of example Scintillation Proximity Assays (SPA), as well as RIA and ELISA Assays.

Human E3 ubiquitin protein ligase may be therefore assayed for inherent pharmacological properties which may be useful to exploit for therapeutic purposes, i.e., administration via gene therapy or otherwise, in vivo, to control the selective elimination of intracellular biomolecules and hence regulate physiology.

various screening assays

The present invention is also directed to methods for screening for compounds which modulate the biological and/or pharmacological activity of the human E3 ubiquitin protein ligase. Compounds which modulate these activities may be DNA, RNA, peptides, proteins, or non-proteinaceous organic molecules. Compounds may modulate the activity by increasing or attenuating the expression of DNA or RNA which encode the biomolecule, or may antagonize or agonize the activity of the human E3 ubiquitin protein ligase itself. Compounds that modulate the expression of DNA or RNA encoding the subunit or the function of the polypeptide may be detected by a variety of assays. The assay may be a simple "yes/no" assay to determine whether there is a change in expression or function. The assay may be made quantitative by comparing the expression or function of a test sample with the levels of expression or function in a standard sample.

The human E3 ubiquitin protein ligase described herein, its immunogenic fragments or oligopeptides can be used for screening therapeutic compounds in any of a variety of drug screening techniques. The fragment employed in such a test may be free in solution, affixed to a solid support, borne on a cell surface, or located intracellularly. The abolition of activity or the formation of binding complexes, between the E3 ubiquitin ligase biomolecule and the agent being tested, may be measured. Accordingly, the present invention provides a method for screening a plurality of compounds for specific binding affinity with the human E3 ubiquitin protein ligase polypeptide or a fragment thereof, comprising providing a plurality of compounds; combining a polypeptide of the present invention or a fragment thereof with each of a plurality of compounds for a time sufficient to allow binding under suitable conditions; and detecting binding of the subunit, or fragment thereof, to each of the plurality of compounds, thereby identifying the compounds which specifically bind the human E3 ubiquitin protein ligase. Compounds that modulate the biological activity of human E3 ubiquitin protein ligase identified in this manner are especially preferred embodiments of the invention. A further embodiment of the present invention is a method of treatment of a patient in need of such treatment for a condition which is mediated by the biological activity of human E3 ubiquitin protein ligase comprising administration of a modulating compound which was identified by means of a method described herein. A further embodiment of the present invention is a method of treatment of a patient in need of such treatment for a condition which is mediated by a pharmacological activity of human E3 ubiquitin protein ligase comprising administration of a modulating compound which was identified by means of a method described herein.

In order to purify an E3 protein ligase polypeptide to measure a binding activity, the source may be a whole cell lysate, prepared by one to three freeze-thaw cycles in the presence of standard protease inhibitors. The protein ligase may be partially or completely purified by standard protein purification methods. Human E3 ubiquitin protein ligase polypeptides described herein may be purified by affinity chromatography using specific antibody described herein or by ligands specific for an epitope tag engineered into the recombinant molecule moreover described herein. The preparation may then be assayed for binding activity as described.

Purified polypeptides comprising the amino acid sequence substantially as depicted in SEQ ID NO:3 are especially preferred embodiments of the present invention.

compounds and methods

Compounds which are identified generally according to methods described, referenced, and contemplated herein that modulate the biological and/or pharmacological activity of human E3 ubiquitin protein ligase (SEQ ID NO:3) are especially preferred embodiments of the present invention. Therefore, as an inherent corollary, a method of the present invention is treatment of a patient in need of such treatment for a condition which is mediated by the biological and/or pharmacological activity of a human E3 ubiquitin protein ligase, comprising administration of a compound that modulates the biological and/or pharmacological activity of a human E3 ubiquitin protein ligase identified by a method described herein.

A further method of the present invention is treatment of a patient in need of such treatment for a condition which is mediated by the biological and/or pharmacological activity of a human E3 ubiquitin protein ligase, comprising administration of the E3 ubiquitin protein ligase substantially as depicted in SEQ ID NO:3 or a pharmacologically active fragment thereof. Therapeutic methods of the present invention also include treatment of a patient in need of such treatment for a condition which is mediated by the biological and/or pharmacological activity of a human E3 ubiquitin protein ligase, comprising administration of a nucleic acid substantially as depicted in SEQ ID NO:1 or a biologically-effective fragment thereof. Therapeutic methods of the present invention furthermore include treatment of a patient in need of such treatment for a condition which is mediated by the biological activity of a human E3 ubiquitin protein ligase, comprising administration of an antisense molecule comprising the complement of the sequence substantially as depicted in SEQ ID NO:2 or a biologically-effective fragment thereof (further discussed infra).

yeast 2-hybrid system

In another embodiment of the invention, a nuleic acid sequence which encodes a human E3 ubiquitin protein ligase molecule substantially as depicted in SEQ ID NO:3 or a biologically and/or pharmacologically active fragment thereof may be ligated to a heterologous sequence to encode a fusion protein, for example, to encode a chimeric human E3 ubiquitin ligase molecule as described herein for expression in hererologous host cells for screening molecules for an ability to modulate human E3 ubiquitin protein ligase biological and/or pharmacological activity, i.e., via binding, association or otherwise.

Chimeric constructs may also be used to express a 'bait', according to methods well known using a yeast two-hybrid system, to identify accessory native peptides that may be associated with the human E3 ubiquitin protein ligase described herein. Fields, S., et al., Trends Genet., 10:286 (1994); Allen, J. B., et al., TIBS, 20:511 (1995). A yeast two-hybrid system has been described wherein protein:protein interactions can be detected using a yeast-based genetic assay via reconstitution of transcriptional activators. Fields, S., Song, O., Nature 340:245 (1989). The two-hybrid system used the ability of a pair of interacting proteins to bring a transcription activation domain into close proximity with a DNA-binding site that regulates the expression of an adjacent reporter gene. Commercially available systems such as the CLONTECH, Matchmaker™ systems and protocols may be used with the present invention. CLONTECH, Palo Alto, Calif. See also, Mendelsohn, A. R., Brent, R., Curr. Op. Biotech., 5:482 (1994); Phizicky. E. M., Fields, S., Microbiological Rev., 59(l):94 (1995); Yang, M., et al., Nucleic Acids Res., 23(7):1152 (1995); Fields, S., Stemglanz, R., TIG, 10(8):286 (1994); and U.S. Pat. No. 5,283,173, *System to Detect Protein-Protein Interactions*, and U.S. Pat. No. 5,468,614, which are incorporated herein by reference.

Modified screening systems, for instance, can be practiced either with a positive readout or with a negative readout such as that in the recently developed versions of "Reverse Y2H" approach. See, e.g., Vidal M, Braun P, Chen E, Boeke J D, Harlow E (1996) *Genetic characterization of a mammalian protein-protein interaction domain by using a yeast reverse two-hybrid system*, Proc Natl Acad Sci U S A 17;93(19):10321–10326; Vidal M, Brachmann R K, Fattaey A, Harlow E, Boeke J D (1996) *Reverse two-hybrid and one-hybrid systems to detect dissociation of protein-protein and DNA-protein interactions*. Proc Natl Acad Sci U S A 17;93(19): 10315–10320; White Mass. (1996) *The yeast two-hybrid system: forward and reverse.* Proc Natl Acad Sci U S A 17;93(19):10001–10003; Leanna C A, Hannink M (1996), *The reverse two-hybrid system: a genetic scheme for selection against specific protein/protein interactions*, Nucleic Acids Res 1;24(17):3341–3347.

antibodies

Monospecific antibodies to the human biomolecule of the present invention (SEQ ID NO:3) are purified from mammalian antisera containing antibodies reactive against the polypeptide or are prepared as monoclonal antibodies reactive with the human E3 ubiquitin protein ligase using the technique of Kohler and Milstein, Nature, 256:495 (1975). Mono-specific antibody as used herein is defined as a single antibody species or multiple antibody species with homogenous binding characteristics for the novel human E3 ubiquitin protein ligase. Homogenous binding as used herein refers to the ability of the antibody species to bind to a specific antigen or epitope. Human E3 ubiquitin protein ligase specific antibodies are raised by immunizing animals such as mice, rats, guinea pigs, rabbits, goats, horses and the like, with rabbits being preferred, with an appropriate concentration of the human E3 ubiquitin protein ligase either with or without an immune adjuvant.

Preimmune serum is collected prior to the first immunization. Each animal receives between about 0.1 mg and about 1000 mg of human E3 ubiquitin protein ligase polypeptide associated with an acceptable immune adjuvant. Such acceptable adjuvants include, but are not limited to, Freund's complete, Freund's incomplete, alum-precipitate, water in oil emulsion containing Corynebacterium parvum and tRNA. The initial immunization consists of a human E3 ubiquitin protein ligase polypeptide in, preferably, Freund's complete adjuvant at multiple sites either subcutaneously (SC), intraperitoneally (IP) or both. Each animal is bled at regular intervals, preferably weekly, to determine antibody titer. The animals may or may not receive booster injections following the initial immunization. Those animals receiving booster injections are generally given an equal amount of the antigen in Freund's incomplete adjuvant by the same route. Booster injections are given at about three week intervals until maximal titers are obtained. At about 7 days after each booster immunization or about weekly after a single immunization, the animals are bled, the serum collected, and aliquots are stored at about −20° C.

Monoclonal antibodies (mAb) reactive with the human E3 ubiquitin protein ligase polypeptide are prepared by immunizing inbred mice, preferably Balb/c, with a human E3 ubiquitin protein ligase polypeptide. The mice are immunized by the IP or SC route with about 0.1 mg to about 10 mg, preferably about 1 mg, of the novel protein ligase polypeptide in about 0.5 ml buffer or saline incorporated in an equal volume of an acceptable adjuvant, as discussed above. Freund's complete adjuvant is preferred. The mice receive an initial immunization on day 0 and are rested for about 3 to about 30 weeks. Immunized mice are given one or more booster immunizations of about 0.1 to about 10 mg of human E3 ubiquitin protein ligase polypeptide in a buffer solution such as phosphate buffered saline by the intravenous (IV) route. Lymphocytes, from antibody positive mice, preferably splenic lymphocytes, are obtained by removing spleens from immunized mice by standard procedures known in the art. Hybridoma cells are produced by mixing the splenic lymphocytes with an appropriate fusion partner, preferably myeloma cells, under conditions which will allow the formation of stable hybridomas. Fusion partners may include, but are not limited to: mouse myelomas P3/NS1/Ag 4-1; MPC-11; S-194 and Sp 2/0, with Sp 2/0 being preferred. The antibody producing cells and myeloma cells are fused in polyethylene glycol, about 1000 molecular weight, at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected from growth positive wells on about days 14, 18, and 21 and are screened for antibody production by an immunoassay such as solid phase immunoradioassay (SPIRA) using a human E3 ubiquitin protein ligase polypeptide as the antigen. The culture fluids are also tested in the Ouchterlony precipitation assay to determine the isotype of the mAb. Hybridoma cells from antibody positive wells are cloned by a technique such as the soft agar technique of MacPherson, Soft Agar Techniques, in Tissue Culture Methods and Applications, Kruse and Paterson, Eds., Academic Press, (1973).

Monoclonal antibodies are produced in vivo by injection of pristane primed Balb/c mice, approximately 0.5 ml per mouse, with about $2 \times 10^6$ to about $6 \times 10^6$ hybridoma cells about 4 days after priming. Ascites fluid is collected at approximately 8–12 days after cell transfer and the monoclonal antibodies are purified by techniques known in the art.

In vitro production of the anti-human E3 ubiquitin protein ligase polypeptide mAb is carried out by growing the hydridoma in DMEM containing about 2% fetal calf serum to obtain sufficient quantities of the specific mAb. The mAb are purified by techniques well known in the art.

diagnostic assays

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. Similar diagnostic assays are used to detect the presence of the human E3 ubiquitin protein ligase in body fluids or tissue and cell extracts.

Diagnostic assays using the human E3 ubiquitin protein ligase polypeptide specific antibodies are useful for the diagnosis of conditions manifested by aberrant forms and/or abnormal levels and/or tissue distribution of the native E3 ubiquitin protein ligase. Diagnostic assays for the human ubiquitin ligase biomolecule of this invention include methods utilizing the antibody and a label to detect the human E3 ubiquitin protein ligase polypeptide in human body fluids, cells, tissues or sections or extracts of such tissues. The polypeptides and antibodies of the present invention may be used with or without modification. Frequently, the polypeptides and antibodies will be labeled by joining them, either covalently or noncovalently, with a reporter molecule, a myriad of which are well-known to those skilled in the art.

A variety of protocols for measuring the human E3 ubiquitin protein ligase polypeptide, using either polyclonal or monoclonal antibodies specific for the respective protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on the human E3 ubiquitin protein ligase is preferred, but a competitive binding assay may be employed. These assays are described, among other places, in Maddox, D. E. et al., J. Exp. Med. 158:1211 (1983); Sites, D. P., et al., *Basic and Clinical Immunology*, Ch.22, 4th Ed., Lange Medical Publications, Los Altos, Calif. (1982); U.S. Pat. No. 3,654,090, No. 3,850,752; and No. 4,016,043.

In order to provide a basis for the diagnosis of disease, normal or standard values for the human E3 ubiquitin protein ligase polypeptide expression must be established. This is accomplished by combining body fluids or cell extracts taken from normal subjects, either animal or human, with antibody to the human ubiquitin ligase biomolecule under conditions suitable for complex formation which are well known in the art. The amount of standard complex formation may be quantified by comparing it with a dilution series of positive controls where a known amount of antibody is combined with known concentrations of purified E3 ubiquitin protein ligase polypeptide. Standard values obtained from normal samples may be compared with values obtained from samples from subjects potentially affected by a disorder or disease related to expression of the human E3 ubiquitin protein ligase. Deviation between standard and subject values establishes the presence of the disease state.

Kits which contain human E3 ubiquitin protein ligase nucleic acid coding region(s), antibodies to a polypeptide, or intact biomolecule may be prepared. Such kits are used to detect sample nucleic acids which hybridize to the human E3 ubiquitin protein ligase nucleic acid coding region(s) contained therein, or to detect the presence of the intact biomolecule or peptide fragments in a sample. Such characterization is useful for a variety of purposes including, but not limited to, diagnosis, forensic analyses and epidemiological studies.

The DNA molecules, RNA molecules, recombinant protein and antibodies of the present invention may be used to screen and measure levels of the human E3 ubiquitin protein ligase DNA, RNA or protein. The recombinant proteins, DNA molecules, RNA molecules and antibodies lend themselves to the formulation of kits suitable for the detection and typing of the novel human E3 ubiquitin protein ligase biomolecule. Such a kit would comprise a compartmentalized carrier suitable to hold in close confinement at least one container. The carrier would further comprise reagents such as recombinant ubiquitin protein ligase or anti-ubiquitin protein ligase antibodies suitable for detecting the novel human E3 ubiquitin protein ligase biomolecule. The carrier may also contain a means for detection such as labeled antigen or enzyme substrates or the like.

Polynucleotide sequences which encode the human E3 ubiquitin protein ligase may be used for the diagnosis of conditions or diseases with which the expression of the human biomolecule is associated. For example, polynucleotide sequences encoding the human E3 ubiquitin protein ligase may be used in hybridization or PCR assays of fluids or tissues from biopsies to detect expression of the biomolecule. The form of such qualitative or quantitative methods may include Southern or Northern analysis, dot blot or other membrane-based technologies; PCR technologies; dip stick, pin, chip and ELISA technologies. All of these techniques are well known in the art and are the basis of many commercially available diagnostic kits. Such assays may also be used to evaluate the efficacy of a particular therapeutic treatment regimen in animal studies, in clinical trials, or in monitoring the treatment of an individual patient. Once disease is established, a therapeutic agent may be administered and a treatment profile generated. Such assays may be repeated on a regular basis to evaluate whether the values in the profile progress toward or return to the normal or standard pattern. Successive treatment profiles may be used to show the efficacy of treatment over a period of several days or several months.

Polynucleotide sequences which encode the human E3 ubiquitin protein ligase may also be employed in analyses to map chromosomal locations, e.g., screening for functional association with disease markers. Moreover the sequences described herein are contemplated for use to identify human sequence polymorphisms and possible association with disease as well as analyses to select optimal sequence from among possible polymorphic sequences for the design of compounds to modulate the biological activity and therefore regulate physiological disorders. Furthermore the sequences are contemplated as screening tools for use in the identification of appropriate human subjects and patients for therapeutic clinical trials.

purification via affinity columns

It is readily apparent to those skilled in the art that methods for producing antibodies may be utilized to produce antibodies specific for human E3 ubiquitin protein ligase polypeptide fragments, or the full-length nascent human polypeptide. Specifically, it is readily apparent to those skilled in the art that antibodies may be generated which are specific for the fully functional biomolecule or fragments thereof.

Human E3 ubiquitin protein ligase antibody affinity columns are made by adding the antibodies to Affigel-10 (Biorad), a gel support which is activated with N hydroxysuccinimide esters such that the antibodies form covalent linkages with the agarose gel bead support. The antibodies are then coupled to the gel via amide bonds with the spacer arm. The remaining activated esters are then quenched with IM ethanolamine HCl (pH 8). The column is washed with water followed by 0.23M glycine HCl (pH 2.6) to remove any non-conjugated antibody or extraneous protein. The column is then equilibrated in phosphate buffered saline (pH 7.3) with appropriate detergent and the cell culture supernatants or cell extracts, for example, containing human E3 ubiquitin protein ligase polypeptide made using appropriate membrane solubilizing detergents are slowly passed through the column. The column is then washed with phosphate buffered saline/detergent until the optical density falls to background, then the protein is eluted with 0.23M glycine-HCl (pH 2.6)/detergent. The purified subunit polypeptide is then dialyzed against phosphate buffered saline/detergent.

Recombinant E3 ubiquitin protein ligase molecules can be separated from other cellular proteins by use of an immunoaffinity column made with monoclonal or polyclonal antibodies specific for the full length nascent human protein, e.g., SEQ ID NO:3, or polypeptide fragments of the biomolecule.

Human E3 ubiquitin protein ligase as described herein may be used to affinity purify biological effectors from native biological materials, e.g. disease tissue. Affinity chromatography techniques are well known to those skilled in the art. The novel polypeptide described herein, e.g., SEQ ID NO:3, or an effective fragment thereof, is fixed to a solid matrix, e.g. CNBr activated Sepharose according to the protocol of the supplier (Pharmacia, Piscataway, N.J.), and a homogenized/buffered cellular solution containing a potential molecule of interest is passed through the column. After washing, the column retains only the biological effector which is subsequently eluted, e.g., using 0.5M acetic acid or a NaCl gradient.

antisense molecules

To enable methods of down-regulating expression of the human E3 ubiquitin protein ligase of the present invention in mammalian cells, an example antisense expression construct containing the complement DNA sequence to the sequence substantially as depicted in SEQ ID NO:2 can be readily constructed for instance using the pREP10 vector (Invitrogen Corporation). Transcripts are expected to inhibit translation of the wild-type E3 ubiquitin protein ligase mRNA in cells transfected with this type construct. Antisense transcripts are effective for inhibiting translation of the native gene transcript, and capable of inducing the effects (e.g., regulation of physiological disorders) herein described. Translation is most effectively inhibited by blocking the mRNA at a site at or near the initiation codon. Thus, oligonucleotides complementary to the corresponding 5'-terminal region of the human E3 ubiquitin protein ligase mRNA transcript (SEQ ID NO:2) are preferred. Secondary or tertiary structure which might interfere with hybridization is minimal in this region. Moreover, sequences that are too distant in the 3' direction from the initiation site can be less effective in hybridizing the mRNA transcripts because of a "read-through" phenomenon whereby the ribosome appears to unravel the antisense/sense duplex to permit translation of the message. Oligonucleotides which are complementary to and hybridizable with any portion of the human E3 ubiquitin protein ligase mRNA are contemplated for therapeutic use.

U.S. Pat. No. 5,639,595, *Identification of Novel Drugs and Reagents*, issued Jun. 17, 1997, wherein methods of identifying oligonucleotide sequences that display in vivo activity are thoroughly described, is herein incorporated by reference. Expression vectors containing random oligonucleotide sequences derived from previously known polynucleotides, e.g., SEQ ID NO:1, are transformed into cells. The cells are then assayed for a phenotype resulting from the desired activity of the oligonucleotide. Once cells with the desired phenotype have been identified, the sequence of the oligonucleotide having the desired activity can be identified. Identification may be accomplished by recovering the vector or by polymerase chain reaction (PCR) amplification and sequencing the region containing the inserted nucleic acid material.

Nucleotide sequences that are complementary to the novel E3 ubiquitin protein ligase polypeptide encoding polynucleotide sequence can be synthesized for antisense therapy. These antisense molecules may be DNA, stable derivatives of DNA such as phosphorothioates or methylphosphonates, RNA, stable derivatives of RNA such as 2'-O-alkylRNA, or other oligonucleotide mimetics. U.S. Pat. No. 5,652,355, *Hybrid Oligonucleotide Phosphorothioates*, issued Jul. 29, 1997, and U.S. Pat. No. 5,652,356, *Inverted Chimeric and Hybrid Oligonucleotides*, issued Jul. 29, 1997, which describe the synthesis and effect of physiologically-stable antisense molecules, are incorporated by reference. Human E3 ubiquitin protein ligase antisense molecules may be introduced into cells by microinjection, liposome encapsulation or by expression from vectors harboring the antisense sequence. Antisense therapy may be particularly useful for the treatment of diseases where it is beneficial to modulate the biological activity and/or pharmacological activity of the human E3 ubiquitin protein ligase described herein.

gene therapy

The human E3 ubiquitin protein ligase polypeptide and variations thereof contemplated herein may administered to a subject via gene therapy. A polypeptide of the present invention may be delivered to the cells of target organs, e.g., hematopoietic cells, in this manner. Conversely, human E3 ubiquitin protein ligase polypeptide antisense gene therapy may be used to modulate the expression of the polypeptide in the same cells of target organs and hence regulate biological and/or pharmacological activity. The human E3 ubiquitin protein ligase coding region can be ligated into viral vectors which mediate transfer of the trans-activator polypeptide nucleic acid by infection of recipient host cells. Suitable viral vectors include retrovirus, adenovirus, adeno-associated virus, herpes virus, vaccinia virus, polio virus and the like. See, e.g., U.S. Pat. No. 5,624,820, *Episomal Expression Vector for Human Gene Therapy*, issued Apr. 29, 1997.

Nucleic acid coding regions of the present invention are incorporated into effective eukaryotic expression vectors, which are directly administered or introduced into somatic cells for gene therapy (a nucleic acid fragment comprising a coding region, preferably mRNA transcripts, may also be administered directly or introduced into somatic cells). See, e.g., U.S. Pat. No. 5,589,466, issued Dec. 31, 1996. Such nucleic acids and vectors may remain episomal or may be incorporated into the host chromosomal DNA as a provirus or portion thereof that includes the gene fusion and appropriate eukaryotic transcription and translation signals, i.e, an effectively positioned RNA polymerase promoter 5' to the transcriptional start site and ATG translation initiation codon of the gene fusion as well as termination codon(s) and transcript polyadenylation signals effectively positioned 3' to the coding region. Alternatively, the human E3 ubiquitin protein ligase DNA can be transferred into cells for gene therapy by non-viral techniques including receptor-mediated targeted DNA transfer using ligand-DNA conjugates or adenovirus-ligand-DNA conjugates, lipofection membrane fusion or direct microinjection. These procedures and variations thereof are suitable for ex vivo, as well as in vivo human gene therapy according to established methods in this art.

PCR diagnostics

The nucleic acid sequence, oligonucleotides, fragments, portions or antisense molecules thereof, may be used in diagnostic assays of body fluids or biopsied tissues to detect the expression level of the human E3 ubiquitin protein ligase. For example, sequences designed from the cDNA sequence SEQ ID NO:1 or sequences comprised in SEQ ID NO:2 can be used to detect the presence of the mRNA transcripts in a patient or to monitor the modulation of transcripts during treatment.

FIG. 7 displays PCR primers, for example, SEQ ID NO:5 and SEQ ID NO:6, which are used to amplify the 2559 bp coding region (SEQ ID NO:2) of the novel human E3 ubiquitin protein ligase from human tissue.

One method for amplification of target nucleic acids, or for later analysis by hybridization assays, is known as the polymerase chain reaction ("PCR") or PCR technique. The PCR technique can be applied to detect sequences of the invention in suspected samples using oligonucleotide primers spaced apart from each other and based on the genetic sequence, e.g., SEQ ID NO:1, set forth herein. The primers are complementary to opposite strands of a double stranded DNA molecule and are typically separated by from about 50 to 450 nucleotides or more (usually not more than 2000 nucleotides). This method entails preparing the specific oligonucleotide primers followed by repeated cycles of target DNA denaturation, primer binding, and extension with a DNA polymerase to obtain DNA fragments of the expected length based on the primer spacing. One example embodiment of the present invention is a diagnostic composition for the identification of a polynucleotide sequence comprising the sequence substantially as depicted in SEQ ID NO:2 comprising the PCR primers substantially as depicted in SEQ ID NO:5 and SEQ ID NO:6 (FIG. 7). The degree of amplification of a target sequence is controlled by the number of cycles that are performed and is theoretically calculated by the simple formula 2n where n is the number of cycles. See, e.g., Perkin Elmer, *PCR Bibliography*, Roche Molecular Systems, Branchburg, N.J.; CLONTECH products, Palo Alto, Calif; U.S. Pat. No. 5,629,158, *Solid Phase Diagnosis of Medical Conditions*, issued May 13, 1997.

compositions

Pharmaceutically useful compositions comprising sequences pertaing to the human E3 ubiquitin protein ligase, DNA, RNA, antisense sequences, or variants and analogs which have biological activity or otherwise compounds which modulate cell physiology identified by methods described herein, may be formulated according to known methods such as by the admixture of a pharmaceutically acceptable carrier. Examples of such carriers and methods of formulation may be found in *Remington's Pharmaceutical Sciences* (Maack Publishing Co, Easton, Pa.). To form a pharmaceutically acceptable composition suitable for effective administration, such compositions will contain an effective amount of the protein, DNA, RNA, or compound modulator.

Therapeutic or diagnostic compositions of the invention are administered to an individual in amounts sufficient to treat or diagnose human physiological disorders, particularly disorders manifested by aberrant forms and/or abnormal levels of the native E3 ubiquitin protein ligase. The effective amount may vary according to a variety of factors such as the individual's condition, weight, sex and age. Other factors include the mode of administration.

The term "chemical derivative" describes a molecule that contains additional chemical moieties which are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as *Remington's Pharmaceutical Sciences.*

Pharmaceutical compositions suitable for use in the present invention include compositions wherein the active ingredients are contained in an effective amount to achieve the intended purpose. The determination of an effective dose is well within the capability of those skilled in the art. The therapeutically effective dose can be estimated initially either in cell culture assays, e.g., of neoplastic cells, or in animal models, usually mice, rabbits, dogs, or pigs. The animal model is also used to achieve a desirable concentration range and route of administration. Such information can then be used to determine useful doses and routes for administration in humans. A therapeutically effective dose refers to that amount of protein or its antibodies, antagonists, or inhibitors which ameliorate the symptoms or condition. The exact dosage is chosen by the individual physician in view of the patient to be treated.

Compounds identified according to the methods disclosed herein may be used alone at appropriate dosages defined by routine testing in order to obtain optimal modulation of a human E3 ubiquitin protein ligase biological activity and/or pharmacological activity, while minimizing any potential toxicity. Co-administration or sequential administration of other agents may be desirable.

The pharmaceutical compositions may be provided to the individual by a variety of routes such as subcutaneous, topical, oral and intramuscular. Administration of pharmaceutical compositions is accomplished orally or parenterally. Methods of parenteral delivery include topical, intra-arterial (directly to the tissue), intramuscular, subcutaneous, intramedullary, intrathecal, intraventricular, intravenous, intraperitoneal, or intranasal administration. The present invention also has the objective of providing suitable topical, oral, systemic and parenteral pharmaceutical formulations for use in the novel methods of treatment of the present invention. The compositions containing compounds identified according to this invention as the active ingredient for use in the modulation of physiological conditions can be administered in a wide variety of therapeutic dosage forms in conventional vehicles for administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound desired can be employed as a E3 ubiquitin protein ligase or variation contemplated herein or human E3 ubiquitin protein ligase modulating agent.

The daily dosage of the products may be varied over a wide range from 0.01 to 1,000 mg per adult human/per day.

For oral administration, the compositions are preferably provided in the form of scored or unscored tablets containing 0.01, 0.05, 0.1, 0.5, 1.0, 2.5, 5.0, 10.0, 15.0, 25.0, and 50.0 milligrams of the active ingredient for the symptomatic adjustment of the dosage to the patient to be treated. An effective amount of the drug is ordinarily supplied at a dosage level of from about 0.0001 mg/kg to about 100 mg/kg of body weight per day. The range is more particularly from about 0.001 mg/kg to 10 mg/kg of body weight per day. Even more particularly, the range varies from about 0.05 to about 1 mg/kg. Of course the dosage level will vary depending upon the potency of the particular compound. Certain compounds will be more potent than others. In addition, the dosage level will vary depending upon the bioavailability of the compound. The more bioavailable and potent the compound, the less compound will need to be administered through any delivery route, including but not limited to oral delivery. The dosages of the modulators desribed herein are adjusted when combined to achieve desired effects. On the other hand, dosages of these various agents may be independently optimized and combined to achieve a synergistic result wherein the pathology is reduced more than it would be if either agent were used alone. Those skilled in the art will employ different formulations for nucleotides than for proteins or their inhibitors. Similarly, delivery of polynucleotides or polypeptides will be specific to particular cells and conditions.

EXAMPLES

Example I

A. ubiquitin thioester conjugation assay for biological activity

Ubiquitin thiol ester formation by the novel human E3 ubiquitin protein ligase (e.g., SEQ ID NO:3) is determined by change in SDS-PAGE mobility of the E3 ligase band (characteristic of thioester formation between ubiquitin and the protein in this gel-shift assay). Reaction mixtures contain 5–10 ng of recombinant E1 (SEQ ID NO:10 (FIG. 12) which is the translated structural coding region of human E1 ubiquitin activating enzyme Ubal), 100 ng of recombinant E2 (SEQ ID NO:11 (FIG. 13) which is the translated structural coding region of the E2 ubiquitin conjugating enzyme E217k) [The human version (Ubc2) is preferred as described by Koken, M., et al., PNAS, 88:8865 (1991)], 200 ng of $^{32}$P-labeled human E3 ligase (SEQ ID NO:3), and 500 ng of GST-ubiquitin in 20 mM Tris-HCl, pH 7.6, 50 mM NaCl, 4 mM ATP, 10 mM MgCl2, and 0.2 mM dithiothreitol for 3 min at 25° C. Human E3 ubiquitin protein ligase reactions are terminated by incubating the mixtures for 15 min at 30° C. in SDS-sample buffer (50 mM Tris-HCl, pH 6.8, 2% SDS, 10% glycerol, and 0.2% bromphenol blue) in the absence of reducing agents and resolved by SDS-PAGE. Radioactively labeled proteins are visualized by autoradiography. Change in the mobility of the E3 ligase band indicates thioester formation in this gel-shift assay. See, alternate techniques, e.g., Huibregtse, J. M., et al., *The HPV-16 E6 and E6-AP Complex Functions as a Ubiquitin-Protein Ligase in the Ubiquitination of p53*, Cell, 75:495 (1995).

Example II ubiquitination assay for biological activity

Physical interaction between specific E2 enzymes (for example, E217k (SEQ ID NO:11 (structural coding region))) [The human version (Ubc2) is preferred as described by Koken, M., et al., PNAS, 88:8865 (1991)] and the novel human E3 ubiquitin protein ligase (e.g., SEQ ID NO:3) characterizes specific functional cooperativity. This assay employs [$^{35}$S]Methionine-labeled proteins synthesized in rabbit reticulocyte lysate in vitro reactions with a coupled transcription/translation kit (PROMEGA, Wis.). Kumar, S., et al., J. Biol. Chem., 272:13548 (1997). Messenger RNA is preferred which originates from hematopoietic cells. Five µl aliquots of in vitro translated hematopoietic cell mRNA is incubated with 5–10 ng of recombinant E1 (SEQ ID NO:10 (FIG. 12) which is the translated structural coding region of human E1 ubiquitin activating enzyme Uba1), approximately 100 ng of E2 (E217k (SEQ ID NO:11 (structural coding region))) [The human version (Ubc2) is preferred as described by Koken, M., et al., PNAS, 88:8865 (1991)] (alternately, UBC2, UBC3, UBC4, UBC5, UBC6, UBC7, UBC8, UBC9, UBC$_{epi}$, UBC$_{bendless}$ (as per citations supra)), 200 ng of the novel human E3 ubiquitin protein ligase (e.g., SEQ ID NO:3), in 20 mM Tris-HCl, pH 7.6, 50 mM NaCl, 4 mM ATP, 10 mM MgCl2, and 0.2 mM dithiothreitol, for 2 hours at 30° C. One mg of glutathione-s-transferase (GST)-ubiquitin fusion protein is then added to 5 ml of translation reaction mixture and incubated for an additional 5 min at room temperature before the reaction is quenched with SDS/PAGE loading buffer. Reactions are terminated after 2 h. at 30° C. by the addition of SDS-sample buffer. Samples are subject to boiling water heat for 5 min, resolved by SDS-PAGE, and visualized by autoradiography. Samples which contain the ubiquitin fusion protein demonstrate shift in the mobility of protein samples that are ubiquitinated.

Example III

Scintillation Proximity Assay (SPA)

Recombinant E1 (using, e.g., SEQ ID NO:10), E2 (using, e.g., SEQ ID NO:11) [The human version (Ubc2) is preferred as described by Koken, M., et al., PNAS, 88:8865 (1991)], and the novel human E3 ubiquitin protein ligase (using, e.g., SEQ ID NO:2) are used to develop a "mix and measure" 96-well SPA (AMERSHAM Scintillation Proximity Assay) by incorporating $^{125}$I-labeled mono-ubiquitin (AMERSHAM) onto a target protein substrate in the presence of ATP and MgCl$_2$. Histone 2A, troponin T, albumin, or (α-actin, for example, may be used as target proteins. The ubiquitinated protein is detected using protein A-labeled SPA beads (AMERSHAM) and a polyclonal antibody to the target protein substrate in question. Both protein A-linked and avidin-linked SPA beads have been successfully used in assays using histone2A and biotinylated histone2A, separately, as substrates.

ubiquitin (UBQ) SPA assay protocol

The reaction mixtures contain 50 mM Tris-HCl (pH 7.5), 2 mM ATP, 5 mM MgCl$_2$, 0.5 mM DTT, (5 ng) recombinant E1 (expressed and isolated from SEQ ID NO:10), (10 ng) recombinant recombinant E2 (expressed and isolated from SEQ ID NO:11) [The human version (Ubc2) is preferred as described by Koken, M., et al., PNAS, 88:8865 (1991)], and (20 ng recombinant the novel human E3 ubiquitin protein ligase (expressed and isolated from SEQ ID NO:2), 1 µg $^{125}$I-Ubiquitin (AMERSHAM, Bucks, UK), and 2µg of biotinylated Histone (SIGMA) to give a final volume of 100 ml. Conjugation assays are performed at room temperature for 2 hours. Following incubation, reactions are terminated by addition of 10 mM EDTA and 0.1 mg/well avidin-linked SPA beads (AMERSHAM).

Final concentrations

|  | Final Concentration in assay |
|---|---|
| E1 | 5 ng/µl |
| E2 | 10 ng/µl |
| E3 | 20 ng/ml |
| Radiolabelled UBQ | 0.02 µCi/well |
| ATP | 2 mM |
| MgCl$_2$ | 5 mM |
| DTT | 0.5 mM |
| Bt-histone | 50 ng/µl |

Stock reagents
  1) E1: @ 9.31 mg/ml
  2) E2: @ 6.68 mg/ml
  3) E3: @ 8.60 mg/ml
  4) $^{125}$I-Ubiquitin: @ 0.1 µCi/µl
  5) ATP: Make at 200 mM ie. 110.2 mg/mil in Tris buffer
  6) MgCl$_2$ : Make at 500 mM ie. 101.7 mg/ml in Tris buffer
  7) DTT: Make at 1M ie. 154.2 mg/ml in Tris buffer
  8) Bt-histone : 2 mg/ml
  Buffer: 50 mM Tris-HCl pH 7.5

Preparation of reagents
Addition 1 (E1/E2/E3)
  (In Tris buffer)
  Dilute E1 1:745
  Dilute E2 1:267
  Dilute E3 1:96
Addition 2 (Label/ATP/MgCl2/DTT/Bt-histone)
Add the following amounts per ml: (Make up with Tris buffer)

|  | µl |
|---|---|
| Label | 4 |
| ATP | 20 |
| MgCl$_2$ | 20 |
| DTT | 1 |
| Bt-histone | 2 | biotinylation of histone2A

Histone2A is biotinylated using BOEHRINGER MANNHEIM kit (cat. no 1418165) according to the manufacturers instructions. Briefly, free amino groups of the target protein (histone2A in this case) are reacted with D-biotinyl-e-aminocaproic acid-N-hydroxysuccinimide ester (biotin-7-NHS) by forming a stable amide bond. Nonreacted biotin-7-NHS is separated on a Sephadex G-25 column. The precise molar concentrations used are 4 mg Histone2A in 1 ml of phosphate buffered saline to which added 20 mg/ml biotin-7-NHS is added. The incubation ss carried out at room temperature for 2 hours with gentle shaking.

Stop Mix (Bead/EDTA)
(Make up with Tris buffer) Add the following amounts per ml:

|  | µl |
|---|---|
| Streptavidin SPA Bead | 600 |
| 500 mM EDTA | 200 |

Method
  Use DYNATECH microlite 1 plates
  Add 10 µl 300 mM EDTA to blank wells

Add 40 μl of Addition 1
Add 50 μl of Addition 2
Incubate at room temperature for 2 hours
Add 50 μl of Stop Mix
Leave overnight and count next day Example IV ELISA assay Target proteins, e.g., histone2A, are fixed to the bottom of a 96-well ELISA plate in the presence of PEI (polyethylimine). The reaction mix: recombinant E1 (expressed and isolated from SEQ ID NO:10), recombinant recombinant E2 (expressed and isolated from SEQ ID NO:11) [The human version (Ubc2) is preferred as described by Koken, M., et al., PNAS, 88:8865 (1991)], and recombinant human E3 ubiquitin protein ligase (expressed and isolated from SEQ ID NO:2), mono-ubiquitin (SIGMA), ATP, and $MgCl_2$, is added to each well. Ubiquitinated target protein is detected using a horseradish peroxidase-linked polyclonal antibody to polyubiquitin. Horseradish peroxidase is detected using ATBS (2,2'-azino-di-[3-ethyl-benzthiazoline solfonate]) and ECL (enhanced chemiluminescence) detection systems. This assay may be used as a high throughput screen or as a secondary screen.

1. Coat plate with 100 μl of desired target protein substrate (e.g., histone2A) diluted in PBS (usually at approx. 1–10 μg/ml). Allow to stand overnight at room temperature or 2 hours at 37° C. (coated plates may be stored for at least 2 weeks at 4° C.).
2. Wash plate 3 times with ELISA Wash Buffer (PBS+ 0.05% Tween-20).
3. Add 150 μl of PBS containing 1% BSA to each well. Incubate at room temperature for 2 hours or at 37 degrees for 1 hour.
4. Wash plate 3 times with ELISA Wash Buffer.
5. Add 100 μl of antibody (e.g., Ub N-19, Santa Cruz, Biotechnology, Calif.) dilutions in PBS containing 1% BSA. Use normal mouse serum as a negative control for ascites and normal rabbit serum as a negative control for rabbit antisera.
6. Cover plate and incubate overnight at room temperature or a minimum of 2 hours at 37° C.
7. Wash plate 3 times with ELISA Wash Buffer.
8. Add 100 μl of the appropriate second antibody enzyme conjugate (e.g., Goat anti-rabbit IgG-HRP) diluted in PBS containing 1% BSA.
9. Cover plate and incubate a minimum of 4 hours at room temperature or 2 hours at 37° C.
10. Wash plate 3 times with ELISA Wash Buffer.
Horseradish Peroxidase (HRP) Substrate (or according to vendor's recommendation)
   25 ml 0.1 Citrate-Phosphate buffer, pH5
   5 g citric acid monohydrate
   7 g Na2HP04 anhydrous
   bring volume to 500 ml with dH20
   Stopping reagent: 6 N H2S04, 50 ul/well
Alkaline phosphatase Substrate (or according to vendor's recommendation)
   1 tube PNPP (100 mg/ml, 0.2 ml)
   20 ml diethanolamine-HCl pH 9.8/1 mM MgCl2
   Stopping reagent: 1 M NaOH, 50 μl/well
Add 100 μl of substrate (orthophenyldiamine+substrate buffer+$H_2O_2$) (6 μl hydrogen peroxide; 10 mg OPD (orthophenyldiamine)); stop reaction when absorbancies in the mid-range of the titration reach about 2.0, or after 1 hour (whichever comes first).

12. Read plate at:
   450 nm—HRP unstopped
   492 nm—HRP stopped
   405 nm—Alkaline phosphatase
(Microplate Spectrophotometer System, Calif.)

See, Takada, K., et al., Eur. J. Biochem., 233:42 (1995); Takada, K., et al., Biochim. Biophys. Acta., 1290:282 (1996).

Example V

Northern blots

Analysis of poly $A^+$RNA's from human tissues is generally carried out using a panel of commercially available pre-blotted RNAs (Clontech Laboratories, Palo Alto, Calif.). Otherwise, Hybond-$N^+$, supplied by Amersham International PLC, AMERSHAM, Bucks, UK, supported nylon-66 membrane with a pore size of 0.45 microns, is used for the immobilisation of nucleic acids by either UV cross linking or dry heat. Probes are labelled with $^{32}p$ by random hexamer priming, and hybridisations are carried out in 0.28M sodium phosphate (pH 7.2), 5×Denharts solution, 10% dextran sulphate, 0.1% SDS at 65° C. Membranes are washed to a final stringency of 0.2× SSC, 0.1% SDS at 65° C. Poly $A^+$ mRNA is prepared directly from ~$1\times10^8$ hematopoietic cells using a FastTrack mRNA isolation kit (INVITROGEN, Carlsbad, Calif.). Total tissue mRNA is prepared via polytron homogenisation in 4M guanidine isothiocyanate, 2.5 mM citrate, 0.5% Saccosyl, 100 mMb-mercaptoethanol, followed by centrifugation through 5.7M CsCl, 25 mM sodium acetate at 135,000 g. Poly-$A^+$ is obtained using FastTrack mRNA isolation kit (INVITROGEN).

SSC 0.15M NaCl+0.015M sodium cirate pH 7.0

Denhart's reagent

Solution containing 0.02% bovine serum albumin, 2% Ficol 400,000 (a non-ionic synthetic polymer of sucrose, dialysed and lyophilised and having an approximate molecular weight of 400,000) and 0.02% polyvinyl pyrrolidone.

All publications and patents mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. A purified polynucleotide comprising a nucleic acid sequence which encodes a polypeptide comprising SEQ ID NO:3.

2. The purified polynucleotide of claim 1 comprising a nucleic acid sequence which encodes a polypeptide comprising a variant of SEQ ID NO:3 wherein cysteine at position 820 is substituted or deleted.

3. An expression vector comprising a polynucleotide selected from the group consisting of the polynucleotides of claims 1 and 2.

4. A host cell transformed with the expression vector of claim 3.

5. A method for producing cells which express a polypeptide, said method comprising a) culturing a host cell according to claim 4 under conditions suitable for the expression of said polypeptide.

6. A method for producing a polypeptide, said method comprising the steps of:

a) culturing a host cell according to claim 4 under conditions suitable for the expression of said polypeptide, and b) recovering polypeptide from the host cell culture.

7. A diagnostic composition for the identification of a polynucleotide comprising SEQ ID NO:2, said diagnostic composition comprised of PCR primers derived from SEQ ID NO:1.

* * * * *

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
        (A) LENGTH: 5359 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:1:

```
GTCGCCGCCG CCCCGAAGTC CCGGTAACCA TGACATTTNA CGGTGGCCTT GTGGNAGACA      60

ACGCCTTAAC CCAAGGAAGT GACTCAAACT GTGAGAACTT CAGGTTTTCC AACCTATTGG     120

TGGTATGTCT GACAGTGGAT CACAACTTGG TTCAATGGGT AGCCTCACCA TGAAATCACA     180

GCTTCAGATC ACTGTCATCT CAGCAAAACT TAAGGAAAAT AAGAAGAATT GGTTTGGACC     240

AAGTCCTTAC GTAGAGGTCA CAGTAGATGG ACAGTCAAAG AAGACAGAAA AATGCAACAA     300

CACAAACAGT CCCAAGTGGA AGCAACCCCT TACAGTTATC GTTACCCCTG TGAGTAAATT     360

ACATTTTCGT GTGTGGAGTC ACCAGACACT GAAATCTGAT GTTTTGTTGG AACTGCTGC     420

ATTAGATATT TATGAAACAT TAAAGTCAAA CAATATGAAA CTTGAAGAAG TAGTTGTGAC     480

TTTGCAGCTT GGAGGTGACA AAGAGCCAAC AGAGACAATA GGAGACTTGT CAATTTGTCT     540

TGATGGGCTA CAGTTAGAGT CTGAAGTTGT TACCAATGGT GAAACTACAT GTTCAGAAAG     600

TGCTTCTCAG AATGATGATG GCTCCAGATC CAAGGATGAA ACAAGAGTGA GCACAAATGG     660

ATCAGATGAC CCTGAAGATG CAGGAGCTGG TGAAAATAGG AGAGTCAGTG GAATAATTC     720

TCCATCACTC TCAAATGGTG GTTTTAAACC TTCTAGACCT CCAAGACCTT CACGACCACC     780

ACCACCCACC CCACGTAGAC CAGCATCTGT CAATGGTTCA CCATCTGCCA CTTCTGAAAG     840

TGATGGGTCT AGTACAGGCT CTCTGCCGCC GACAAATACA AATACAAATA CATCTGAAGG     900

AGCAACATCT GGATTAATAA TTCCTCTTAC TATATCTGGA GGCTCAGGCC CTAGGCCATT     960

AAATCCTGTA ACTCAAGCTC CCTTGCCACC TGGTTGGGAG CAGAGAGTGG ACCAGCACGG    1020

GCGAGTTTAC TATGTAGATC ATGTTGAGAA AGAACAACAA TGGGATAGAC CAGAACCTCT    1080

ACCTCCTGGC TGGGAACGGC GGGTTGACAA CATGGGACGT ATTTATTATG TTGACCATTT    1140

CACAAGAACA CAACGTGGC AGAGGCCAAC ACTGGAATCC GTCCGGAACT ATGAACAATG    1200

GCAGCTACAG CGTAGTCAGC TTCAAGGAGC AATGCAGCAG TTTAACCAGA GATTCATTTA    1260

TGGGAATCAA GATTTATTTG CTACATCACA AGTAAAGAA TTTGATCCTC TTGGTCSATT    1320

GCCACCTGGA TGGGAGAAGA GAACAGACAG CAATGGCAGA GTATATTTCG TCAACCACAA    1380

CACACGAATT ACACAATGGG AAGACCCCAG AAGTCAAGGT CAATTAAATG AAAAGCCCTT    1440

ACCTGAAGGT TGGGAAATGA GATTCACAGT GGATGGAATT CCATATTTTG TGGACCACAA    1500

TAGAAGAACT ACCACCTATA TAGATCCCCG CACAGGAAAA TCTGCCCTAG ACAATGGACC    1560

TCAGATAGCC TATGTTCGGG ACTTCAAAGC AAAGGTTCAG TATTTCCGGT TCTGGTGTCA    1620

GCAACTGGCC ATGCCACAGC ACATAAAGAT TACAGTGACA AGAAAAACAT GTTTGAGGA    1680

TTCCTTTCAA CAGATAATGA GCTTCAGTCC CCAAGATCTG CGAAGACGTT TGTGGGTGAT    1740

TTTTCCAGGA GAAGAAGGTT TAGATTATGG AGGTGTAGCA AGAGAATGGT TCTTTCTTTT    1800
```

-continued

```
GTCACATGAA GTGTTGAACC CAATGTATTG CCTGTTTGAA TATGCAGGGA AGGATAACTA      1860

CTGCTTGCAG ATAAACCCCG CTTCTTACAT CAATCCAGAT CACCTGAAAT ATTTTCGTTT      1920

TATTGGCAGA TTTATTGCCA TGGCTCTGTT CCATGGGAAA TTCATAGACA CGGGTTTTTC      1980

TTTACCATTC TATAAGCGTA TCTTGAACAA ACCAGTTGGA CTCAAGGATT TAGAATCTAT      2040

TGATCCAGAA TTTTACAATT CTCTCATCTG GGTTAAGGAA ACAATATTG AGGAATGTGA       2100

TTTGGAAATG TACTTCTCCG TTGACAAAGA AATTCTAGGT GAAATTAAGA GTCATGATCT      2160

GAAACCTAAT GGTGGCAATA TTCTTGTAAC AGAAGAAAAT AAAGAGGAAT ACATCAGAAT      2220

GGTAGCTGAG TGGAGGTTGT CTCGAGGTGT TGAAGAACAG ACACAAGCTT TCTTTGAAGG      2280

CTTTAATGAA ATTCTTCCCC AGCAATATTT GCAATACTTT GATGCAAAGG AATTAGAGGT      2340

CCTTTTATGT GGAATGCAAG AGATTGATTT GAATGACTGG CAAAGACATG CCATCTACCG      2400

TCATTATGCA AGGACCAGCA AACAAATCAT GTGGTTTTGG CAGTTTGTTA AAGAAATTGA      2460

TAATGAGAAG AGAATGAGAC TTCTGCAGTT TGTTACTGGA ACCTGCCGAT TGCCAGTAGG      2520

AGGATTTGCT GATCTCATGG GGAGCAATGG ACCACAGAAA TTCTGCATTG AAAAAGTTGG      2580

GAAAGAAAAT TGGCTACCCA GAAGTCATAC CTGTTTTAAT CGCCTGGACC TGCCACCATA      2640

CAAGAGCTAT GAGCAACTGA AGGAAAAGCT GTTGTTTGCC ATAGAAGAAA CAGAAGGATT      2700

TGGACAAGAG TAACTTCTGA GAACTTGCAC CATGAATGGG CAAGAACTTA TTTGCAATGT      2760

TTGTCCTTCT CTGCCTGTTG CACATCTTGT AAAATTGGAC AATGGCTCTT TAGAGAGTTA      2820

TCTGAGTGTA AGTAAATTAA TGTTCTCATT TAGATTTATC TCCCAGTGAT TTCTACTCAG      2880

CGTTTCCAGA AATCAGGTCT GCAAATGACT AGTCAGAACC TTGCTTAACA TGAGATTTTA      2940

ACACAACAAT GAAATTTGCC TTGTCTTATT CCACTAGTTT ATTCCTTTAA CAACAATATT      3000

TTATRTGTRT CAAAAGTCTC ACTTGGGAGT AGTGTTTTTT TCTTTTAGAC ATTCTGCAGA      3060

CATGCAGGGA AGTCCTTTGG TAACTGCAAT ATACAAGATT TTCCTATTAA GCCTCTTGGT      3120

AAGAGGCATT TGTTAAAAGT GCAAGCTTAC TCCTGCTTCT GGGGATGTGA GCAAAATTCG      3180

GGCTTGTGTT CTCCCTCTCA TTTTAGTCTG ACTTGACTAT TGTTTTTCCT TTCTGGCGCA      3240

TGAATCCATA CATCATTCCT GGAAGTGAGG CAAGACTCTT GCATCTCTAC AAAGTAGTTT      3300

TGTCAATTTG AATTCAGGGA AAAGTTGGTC ACAGCCTGCA AATGACTTCA TTTGGAAGTC      3360

TGATTGTTTC AGTTGCCTGA CAAATACTAC ACTTTACAAA CAATGTTAAC ACTGTGATTC      3420

CTTCATTGTT TTAAGAAGTT AACCTAGGGC CGGGCATGGT GGCTCATACC TGTAATCCTA      3480

GCACTCTGGG AGGCCGAGGC AGGAGGATCC CTTTAGCCCA GGAGTTAAAG ACCAGCCTGG      3540

GCAACATAGG GAGACCCTGT CTTTTTTTTG GGCAGCGTGG TGGGGATAA ATAAAWAAAA       3600

RRAAAAAAAA CKTAGCCTAG AATTAGAATT AATTTAATTG AATTCATCTA AAGATGTCTC      3660

TGGTGATTTT TATATGTTCC GCTATATAAT TGATGCTTTA TAGTTTTATC ATAATCCAAC      3720

AACTTCAGTT ATATTTAATT ATTGTTAAGG AGTTTAAGAC TAGAAAGACT AGAGTGCTTT      3780

CTAGTCCAAA TAGAGGTCAG TGAAACAGCT TTTGACATCA GATTTTCATT TGAGAGGGAG      3840

AGCTGTGGTA CTGGCTAAAA AGAAAGGAAG ATAACATCCA GTAACCACAG GAATATATTC      3900

TCTGTGAATT AAAAGTCTTC AAAGTTATCA TTTCTCTGAC ATATGTTGGA GTAGTCATTT      3960

CCATTCTTTA CATTGTCATG AACTGGATTG ATAACCCTCA TCTGCAATAT TTTCACCCCT      4020

AAAATTTTTA ACAGGGTTTC CTTTTTTTCT CACGACTATT TAAGTTTAGA TTGCTCCATT      4080

ATTAACTGAT TAATGCACTT TGAAGTTCTC TGGAATTAAT TATTTAACT TGGCCTAGCT       4140

TCGACTGTCA AGGTGGCTGT TATAAATTTG ACTTCATTGG CAGTGGATGA AGCCTAAGCC      4200
```

```
AGCTGAGTCT CTATCATAGC TGAACCCTGA GGACAGCCTC ATAGCTCATG TATCAGGGAC    4260

TTTTGCCACA TTTCAGAGGC ATAGCATGAA CAAGTAATAT TAAGCCAAGA ATAAGCAGCA    4320

GAACCCTGTT CCATATGGAA AAAGAAAAA CAATTTTTTG TCCCTAATGT TCTTCCTTTT    4380

ACATCCTGGA ACAACAATAA AAACATTTTT TTAAACTTGT CTACTGTAAG ATACTGCCAT    4440

CATAAAGCAG AGACTTACAT GAGTGAAAGG GTTGCCTCAT CAAGCAGCTC AGTGTAAATG    4500

GGGAGGCTAG GCTCTCCCCA GCCCTATGGT TTTTTTATTT CATGTACCCC AGGAAATACT    4560

GTGTGGTTTC TAAAAGCCCT GGTTGTTAAA AGTAGGGACT CTGCCTTTTT GTTGGTAGGG    4620

AGAAAAAACG CTATTGCTTT GTCTTACAGA GCGAATGTCT GCCAACTACC CGTTCATTAT    4680

ATAAGTCTGA ACTTGGTAAT ATATGGCTAA TGAAGATTAA GCCCTCTATA AAGACTTCCT    4740

GTTGAGGTGA ATTCTCATAC TGAAATGTAG TTACCTACAA TATTTACTAG AGATTTATGA    4800

AATTAAATTA AGAGATAATG TAAGAAAATA CATTTTTTTT GGTTCTATAT AATGCTTCAT    4860

GATTCATTTA GGGACCTAGA AATATTGTGT GAAAATATAT AAATATCACC CAAAAGGCTT    4920

TCTGCCCTAT ATTTTTAAAA TACAGAATAG TTATATTTGA AGTAGCCCTG GCCCTAGTTC    4980

TATAGGGCTT GGCTATTTAA TATTTTTATG GAAGAAGTGT TTAGTTCTGG AAAAGGTAAA    5040

TGCTTGTATA TATATTTTTG CAGCCTGGGA TCTCCCTACT CCATTTTTTC CTTTAATTTA    5100

AGTGGCCACA TGTATATGTC TTCCCTGCTG TGTTAGGAAA ATGGGGGCTG GATATCCCAA    5160

GAATCAGAGG TTATATAAAA ATACTGCAAA TAGACCGCAG ACATAAATAT CTACCAAATG    5220

CTATCTTAAA TTTTGGTCCA AACTGAACAT ATGGAAATAG ATTTATTGTA AGTATTTACT    5280

TAGAGCTTTT TCTTAAATCT GAACTAACTT GCTTTTAGAA GTCTTTTTCT TTGTAAGCAT    5340

TGTAAATGCT AATAAATCC                                                 5359

(2) INFORMATION FOR SEQ ID NO:2:

(i) SEQUENCE CHARACTERISTICS:
         (A) LENGTH: 2559 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:2:

ATGGGTAGCC TCACCATGAA ATCACAGCTT CAGATCACTG TCATCTCAGC AAAACTTAAG      60

GAAAATAAGA AGAATTGGTT TGGACCAAGT CCTTACGTAG AGGTCACAGT AGATGGACAG    120

TCAAAGAAGA CAGAAAAATG CAACAACACA AACAGTCCCA AGTGGAAGCA ACCCCTTACA    180

GTTATCGTTA CCCCTGTGAG TAAATTACAT TTTCGTGTGT GGAGTCACCA GACACTGAAA    240

TCTGATGTTT TGTTGGGAAC TGCTGCATTA GATATTTATG AAACATTAAA GTCAAACAAT    300

ATGAAACTTG AAGAAGTAGT TGTGACTTTG CAGCTTGGAG GTGACAAAGA GCCAACAGAG    360

ACAATAGGAG ACTTGTCAAT TTGTCTTGAT GGGCTACAGT TAGAGTCTGA AGTTGTTACC    420

AATGGTGAAA CTACATGTTC AGAAAGTGCT TCTCAGAATG ATGATGGCTC CAGATCCAAG    480

GATGAAACAA GAGTGAGCAC AAATGGATCA GATGACCCTG AAGATGCAGG AGCTGGTGAA    540

AATAGGAGAG TCAGTGGGAA TAATTCTCCA TCACTCTCAA ATGGTGGTTT TAAACCTTCT    600

AGACCTCCAA GACCTTCACG ACCACCACCA CCCACCCCAC GTAGACCAGC ATCTGTCAAT    660

GGTTCACCAT CTGCCACTTC TGAAAGTGAT GGGTCTAGTA CAGGCTCTCT GCCGCCGACA    720

AATACAAATA CAAATACATC TGAAGGAGCA ACATCTGGAT TAATAATTCC TCTTACTATA    780

TCTGGAGGCT CAGGCCCTAG GCCATTAAAT CCTGTAACTC AAGCTCCCTT GCCACCTGGT    840
```

```
TGGGAGCAGA GAGTGGACCA GCACGGGCGA GTTTACTATG TAGATCATGT TGAGAAAAGA      900

ACAACATGGG ATAGACCAGA ACCTCTACCT CCTGGCTGGG AACGGCGGGT TGACAACATG      960

GGACGTATTT ATTATGTTGA CCATTTCACA AGAACAACAA CGTGGCAGAG GCCAACACTG     1020

GAATCCGTCC GGAACTATGA ACAATGGCAG CTACAGCGTA GTCAGCTTCA AGGAGCAATG     1080

CAGCAGTTTA ACCAGAGATT CATTTATGGG AATCAAGATT TATTTGCTAC ATCACAAAGT     1140

AAAGAATTTG ATCCTCTTGG TCCATTGCCA CCTGGATGGG AGAAGAGAAC AGACAGCAAT     1200

GGCAGAGTAT ATTTCGTCAA CCACAACACA CGAATTACAC AATGGGAAGA CCCCAGAAGT     1260

CAAGGTCAAT TAAATGAAAA GCCCTTACCT GAAGGTTGGG AAATGAGATT CACAGTGGAT     1320

GGAATTCCAT ATTTTGTGGA CCACAATAGA AGAACTACCA CCTATATAGA TCCCCGCACA     1380

GGAAAATCTG CCCTAGACAA TGGACCTCAG ATAGCCTATG TTCGGGACTT CAAAGCAAAG     1440

GTTCAGTATT TCCGGTTCTG GTGTCAGCAA CTGGCCATGC CACAGCACAT AAAGATTACA     1500

GTGACAAGAA AAACATTGTT TGAGGATTCC TTTCAACAGA TAATGAGCTT CAGTCCCCAA     1560

GATCTGCGAA GACGTTTGTG GGTGATTTTT CCAGGAGAAG AAGGTTTAGA TTATGGAGGT     1620

GTAGCAAGAG AATGGTTCTT TCTTTTGTCA CATGAAGTGT TGAACCCAAT GTATTGCCTG     1680

TTTGAATATG CAGGGAAGGA TAACTACTGC TTGCAGATAA ACCCCGCTTC TTACATCAAT     1740

CCAGATCACC TGAAATATTT TCGTTTTATT GGCAGATTTA TTGCCATGGC TCTGTTCCAT     1800

GGGAAATTCA TAGACACGGG TTTTTCTTTA CCATTCTATA AGCGTATCTT GAACAAACCA     1860

GTTGGACTCA AGGATTTAGA ATCTATTGAT CCAGAATTTT ACAATTCTCT CATCTGGGTT     1920

AAGGAAAACA ATATTGAGGA ATGTGATTTG GAAATGTACT TCTCCGTTGA CAAAGAAATT     1980

CTAGGTGAAA TTAAGAGTCA TGATCTGAAA CCTAATGGTG GCAATATTCT TGTAACAGAA     2040

GAAAATAAAG AGGAATACAT CAGAATGGTA GCTGAGTGGA GGTTGTCTCG AGGTGTTGAA     2100

GAACAGACAC AAGCTTTCTT TGAAGGCTTT AATGAAATTC TTCCCCAGCA ATATTTGCAA     2160

TACTTTGATG CAAAGGAATT AGAGGTCCTT TTATGTGGAA TGCAAGAGAT TGATTTGAAT     2220

GACTGGCAAA GACATGCCAT CTACCGTCAT TATGCAAGGA CCAGCAAACA AATCATGTGG     2280

TTTTGGCAGT TTGTTAAAGA AATTGATAAT GAGAAGAGAA TGAGACTTCT GCAGTTTGTT     2340

ACTGGAACCT GCCGATTGCC AGTAGGAGGA TTTGCTGATC TCATGGGGAG CAATGGACCA     2400

CAGAAATTCT GCATTGAAAA AGTTGGGAAA GAAAATTGGC TACCCAGAAG TCATACCTGT     2460

TTTAATCGCC TGGACCTGCC ACCATACAAG AGCTATGAGC AACTGAAGGA AAAGCTGTTG     2520

TTTGCCATAG AAGAAACAGA AGGATTTGGA CAAGAGTAA                          2559

(2) INFORMATION FOR SEQ ID NO:3:

(i) SEQUENCE CHARACTERISTICS:
        (A) LENGTH: 852 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:3:

Met Gly Ser Leu Thr Met Lys Ser Gln Leu Gln Ile Thr Val Ile Ser
 1               5                  10                  15

Ala Lys Leu Lys Glu Asn Lys Lys Asn Trp Phe Gly Pro Ser Pro Tyr
                20                  25                  30

Val Glu Val Thr Val Asp Gly Gln Ser Lys Lys Thr Glu Lys Cys Asn
            35                  40                  45
```

-continued

```
Asn Thr Asn Ser Pro Lys Trp Lys Gln Pro Leu Thr Val Ile Val Thr
         50                  55                  60

Pro Val Ser Lys Leu His Phe Arg Val Trp Ser His Gln Thr Leu Lys
 65                  70                  75                  80

Ser Asp Val Leu Leu Gly Thr Ala Ala Leu Asp Ile Tyr Glu Thr Leu
                     85                  90                  95

Lys Ser Asn Asn Met Lys Leu Glu Glu Val Val Thr Leu Gln Leu
                100                 105                 110

Gly Gly Asp Lys Glu Pro Thr Glu Thr Ile Gly Asp Leu Ser Ile Cys
             115                 120                 125

Leu Asp Gly Leu Gln Leu Glu Ser Glu Val Val Thr Asn Gly Glu Thr
         130                 135                 140

Thr Cys Ser Glu Ser Ala Ser Gln Asn Asp Asp Gly Ser Arg Ser Lys
145                 150                 155                 160

Asp Glu Thr Arg Val Ser Thr Asn Gly Ser Asp Pro Glu Asp Ala
                 165                 170                 175

Gly Ala Gly Glu Asn Arg Arg Val Ser Gly Asn Asn Ser Pro Ser Leu
             180                 185                 190

Ser Asn Gly Gly Phe Lys Pro Ser Arg Pro Arg Pro Ser Arg Pro
         195                 200                 205

Pro Pro Pro Thr Pro Arg Arg Pro Ala Ser Val Asn Gly Ser Pro Ser
210                 215                 220

Ala Thr Ser Glu Ser Asp Gly Ser Ser Thr Gly Ser Leu Pro Pro Thr
225                 230                 235                 240

Asn Thr Asn Thr Asn Thr Ser Glu Gly Ala Thr Ser Gly Leu Ile Ile
                 245                 250                 255

Pro Leu Thr Ile Ser Gly Gly Ser Gly Pro Arg Pro Leu Asn Pro Val
                 260                 265                 270

Thr Gln Ala Pro Leu Pro Pro Gly Trp Glu Gln Arg Val Asp Gln His
             275                 280                 285

Gly Arg Val Tyr Tyr Val Asp His Val Glu Lys Arg Thr Thr Trp Asp
         290                 295                 300

Arg Pro Glu Pro Leu Pro Pro Gly Trp Glu Arg Arg Val Asp Asn Met
305                 310                 315                 320

Gly Arg Ile Tyr Tyr Val Asp His Phe Thr Arg Thr Thr Trp Gln
                 325                 330                 335

Arg Pro Thr Leu Glu Ser Val Arg Asn Tyr Glu Gln Trp Gln Leu Gln
             340                 345                 350

Arg Ser Gln Leu Gln Gly Ala Met Gln Gln Phe Asn Gln Arg Phe Ile
         355                 360                 365

Tyr Gly Asn Gln Asp Leu Phe Ala Thr Ser Gln Ser Lys Glu Phe Asp
         370                 375                 380

Pro Leu Gly Pro Leu Pro Pro Gly Trp Glu Lys Arg Thr Asp Ser Asn
385                 390                 395                 400

Gly Arg Val Tyr Phe Val Asn His Asn Thr Arg Ile Thr Gln Trp Glu
                 405                 410                 415

Asp Pro Arg Ser Gln Gly Gln Leu Asn Glu Lys Pro Leu Pro Glu Gly
             420                 425                 430

Trp Glu Met Arg Phe Thr Val Asp Gly Ile Pro Tyr Phe Val Asp His
             435                 440                 445

Asn Arg Arg Thr Thr Thr Tyr Ile Asp Pro Arg Thr Gly Lys Ser Ala
450                 455                 460

Leu Asp Asn Gly Pro Gln Ile Ala Tyr Val Arg Asp Phe Lys Ala Lys
```

```
              465                 470                 475                 480
Val Gln Tyr Phe Arg Phe Trp Cys Gln Gln Leu Ala Met Pro Gln His
                    485                 490                 495
Ile Lys Ile Thr Val Thr Arg Lys Thr Leu Phe Glu Asp Ser Phe Gln
                500                 505                 510
Gln Ile Met Ser Phe Ser Pro Gln Asp Leu Arg Arg Arg Leu Trp Val
            515                 520                 525
Ile Phe Pro Gly Glu Glu Gly Leu Asp Tyr Gly Gly Val Ala Arg Glu
        530                 535                 540
Trp Phe Phe Leu Leu Ser His Glu Val Leu Asn Pro Met Tyr Cys Leu
545                 550                 555                 560
Phe Glu Tyr Ala Gly Lys Asp Asn Tyr Cys Leu Gln Ile Asn Pro Ala
                565                 570                 575
Ser Tyr Ile Asn Pro Asp His Leu Lys Tyr Phe Arg Phe Ile Gly Arg
                580                 585                 590
Phe Ile Ala Met Ala Leu Phe His Gly Lys Phe Ile Asp Thr Gly Phe
            595                 600                 605
Ser Leu Pro Phe Tyr Lys Arg Ile Leu Asn Lys Pro Val Gly Leu Lys
        610                 615                 620
Asp Leu Glu Ser Ile Asp Pro Glu Phe Tyr Asn Ser Leu Ile Trp Val
625                 630                 635                 640
Lys Glu Asn Asn Ile Glu Glu Cys Asp Leu Glu Met Tyr Phe Ser Val
                645                 650                 655
Asp Lys Glu Ile Leu Gly Glu Ile Lys Ser His Asp Leu Lys Pro Asn
                660                 665                 670
Gly Gly Asn Ile Leu Val Thr Glu Glu Asn Lys Glu Glu Tyr Ile Arg
            675                 680                 685
Met Val Ala Glu Trp Arg Leu Ser Arg Gly Val Glu Glu Gln Thr Gln
        690                 695                 700
Ala Phe Phe Glu Gly Phe Asn Glu Ile Leu Pro Gln Gln Tyr Leu Gln
705                 710                 715                 720
Tyr Phe Asp Ala Lys Glu Leu Glu Val Leu Leu Cys Gly Met Gln Glu
                725                 730                 735
Ile Asp Leu Asn Asp Trp Gln Arg His Ala Ile Tyr Arg His Tyr Ala
                740                 745                 750
Arg Thr Ser Lys Gln Ile Met Trp Phe Trp Gln Phe Val Lys Glu Ile
            755                 760                 765
Asp Asn Glu Lys Arg Met Arg Leu Leu Gln Phe Val Thr Gly Thr Cys
        770                 775                 780
Arg Leu Pro Val Gly Gly Phe Ala Asp Leu Met Gly Ser Asn Gly Pro
785                 790                 795                 800
Gln Lys Phe Cys Ile Glu Lys Val Gly Lys Glu Asn Trp Leu Pro Arg
                805                 810                 815
Ser His Thr Cys Phe Asn Arg Leu Asp Leu Pro Pro Tyr Lys Ser Tyr
                820                 825                 830
Glu Gln Leu Lys Glu Lys Leu Leu Phe Ala Ile Glu Glu Thr Glu Gly
            835                 840                 845
Phe Gly Gln Glu
    850

(2) INFORMATION FOR SEQ ID NO:4:

(i) SEQUENCE CHARACTERISTICS:
        (A) LENGTH: 854 amino acids
        (B) TYPE: amino acid
```

(C) STRANDEDNESS: unknown
(D) TOPOLOGY: unknown (ii) MOLECULE TYPE: peptide (xi) SEQUENCE DESCRIPTION: SEQ ID NO:4:

```
Met Gly Ser Leu Thr Met Lys Ser Gln Leu Gln Ile Thr Val Ile Ser
 1               5                  10                  15

Ala Lys Leu Lys Glu Asn Lys Lys Asn Trp Phe Gly Pro Ser Pro Tyr
                20                  25                  30

Val Glu Val Thr Val Asp Gly Gln Ser Lys Lys Thr Glu Lys Cys Asn
                35                  40                  45

Asn Thr Asn Ser Pro Lys Trp Lys Gln Pro Leu Thr Val Ile Val Thr
    50                  55                  60

Pro Thr Ser Lys Leu Cys Phe Arg Val Trp Ser His Gln Thr Leu Lys
65                  70                  75                  80

Ser Asp Val Leu Leu Gly Thr Ala Gly Leu Asp Ile Tyr Glu Thr Leu
                    85                  90                  95

Lys Ser Asn Asn Met Lys Leu Glu Glu Val Val Met Thr Leu Gln Leu
                100                 105                 110

Val Gly Asp Lys Glu Pro Thr Glu Thr Met Gly Asp Leu Ser Val Cys
                115                 120                 125

Leu Asp Gly Leu Gln Val Glu Ala Glu Val Val Thr Asn Gly Glu Thr
    130                 135                 140

Ser Cys Ser Glu Ser Thr Thr Gln Asn Asp Asp Gly Cys Arg Thr Arg
145                 150                 155                 160

Asp Asp Thr Arg Val Ser Thr Asn Gly Ser Glu Asp Pro Glu Val Ala
                165                 170                 175

Ala Ser Gly Glu Asn Lys Arg Ala Asn Gly Asn Asn Ser Pro Ser Leu
                180                 185                 190

Ser Asn Gly Gly Phe Lys Pro Ser Arg Pro Pro Arg Pro Ser Arg Pro
                195                 200                 205

Pro Pro Pro Thr Pro Arg Arg Pro Ala Ser Val Asn Gly Ser Pro Ser
        210                 215                 220

Thr Asn Ser Asp Ser Asp Gly Ser Ser Thr Gly Ser Leu Pro Pro Thr
225                 230                 235                 240

Asn Thr Asn Val Asn Thr Ser Thr Ser Glu Gly Ala Thr Ser Gly Leu
                245                 250                 255

Ile Ile Pro Leu Thr Ile Ser Gly Gly Ser Gly Pro Arg Pro Leu Asn
                260                 265                 270

Thr Val Ser Gln Ala Pro Leu Pro Pro Gly Trp Glu Gln Arg Val Asp
                275                 280                 285

Gln His Gly Arg Val Tyr Tyr Val Asp His Val Glu Lys Arg Thr Thr
        290                 295                 300

Trp Asp Arg Pro Glu Pro Leu Pro Pro Gly Trp Glu Arg Arg Val Asp
305                 310                 315                 320

Asn Met Gly Arg Ile Tyr Tyr Val Asp His Phe Thr Arg Thr Thr Thr
                325                 330                 335

Trp Gln Arg Pro Thr Leu Glu Ser Val Arg Asn Tyr Glu Gln Trp Gln
                340                 345                 350

Leu Gln Arg Ser Gln Leu Gln Gly Ala Met Gln Gln Phe Asn Gln Arg
                355                 360                 365

Phe Ile Tyr Gly Asn Gln Asp Leu Phe Ala Thr Ser Gln Asn Lys Glu
    370                 375                 380

Phe Asp Pro Leu Gly Pro Leu Pro Pro Gly Trp Glu Lys Arg Thr Asp
```

```
                385                 390                 395                 400
Ser Asn Gly Arg Val Tyr Phe Val Asn His Asn Thr Arg Ile Thr Gln
                405                 410                 415

Trp Glu Asp Pro Arg Ser Gln Gly Gln Leu Asn Glu Lys Pro Leu Pro
                420                 425                 430

Glu Gly Trp Glu Met Arg Phe Thr Val Asp Gly Ile Pro Tyr Phe Val
                435                 440                 445

Asp His Asn Arg Arg Ala Thr Thr Tyr Ile Asp Pro Arg Thr Gly Lys
450                 455                 460

Ser Ala Leu Asp Asn Gly Pro Gln Ile Ala Tyr Val Arg Asp Phe Lys
465                 470                 475                 480

Ala Lys Val Gln Tyr Phe Arg Phe Trp Cys Gln Gln Leu Ala Met Pro
                485                 490                 495

Gln His Ile Lys Ile Thr Val Thr Arg Lys Thr Leu Phe Glu Asp Ser
                500                 505                 510

Phe Gln Gln Ile Met Ser Phe Ser Pro Gln Asp Leu Arg Arg Arg Leu
                515                 520                 525

Trp Val Ile Phe Pro Gly Glu Glu Gly Leu Asp Tyr Gly Gly Val Ala
                530                 535                 540

Arg Glu Trp Phe Phe Leu Leu Ser His Glu Val Leu Asn Pro Met Tyr
545                 550                 555                 560

Cys Leu Phe Glu Tyr Ala Gly Lys Asp Asn Tyr Cys Leu Gln Ile Asn
                565                 570                 575

Pro Ala Ser Tyr Ile Asn Pro Asp His Leu Lys Tyr Phe Arg Phe Ile
                580                 585                 590

Gly Arg Phe Ile Ala Met Ala Leu Phe His Gly Lys Phe Ile Asp Thr
                595                 600                 605

Gly Phe Ser Leu Pro Phe Tyr Lys Arg Ile Leu Asn Lys Pro Val Gly
                610                 615                 620

Leu Lys Asp Leu Glu Ser Ile Asp Pro Glu Phe Tyr Asn Ser Leu Ile
625                 630                 635                 640

Trp Val Lys Glu Asn Asn Ile Glu Glu Cys Gly Leu Glu Met Tyr Phe
                645                 650                 655

Ser Val Asp Lys Glu Ile Leu Gly Glu Ile Lys Ser His Asp Leu Lys
                660                 665                 670

Pro Asn Gly Gly Asn Ile Leu Val Thr Glu Glu Asn Lys Glu Glu Tyr
                675                 680                 685

Ile Arg Met Val Ala Glu Trp Arg Leu Ser Arg Gly Val Glu Glu Gln
                690                 695                 700

Thr Gln Ala Phe Phe Glu Gly Phe Asn Glu Ile Leu Pro Gln Gln Tyr
705                 710                 715                 720

Leu Gln Tyr Phe Asp Ala Lys Glu Leu Glu Val Leu Leu Cys Gly Met
                725                 730                 735

Gln Glu Ile Asp Leu Asn Asp Trp Gln Arg His Ala Ile Tyr Arg His
                740                 745                 750

Tyr Thr Arg Thr Ser Lys Gln Ile Met Trp Phe Trp Gln Phe Val Lys
                755                 760                 765

Glu Ile Asp Asn Glu Lys Arg Met Arg Leu Leu Gln Phe Val Thr Gly
                770                 775                 780

Thr Cys Arg Leu Pro Val Gly Gly Phe Ala Asp Leu Met Gly Ser Asn
785                 790                 795                 800

Gly Pro Gln Lys Phe Cys Ile Glu Lys Val Gly Lys Glu Asn Trp Leu
                805                 810                 815
```

```
Pro Arg Ser His Thr Cys Phe Asn Arg Leu Asp Leu Pro Pro Tyr Lys
        820                 825                 830
```

```
Ser Tyr Glu Gln Leu Lys Glu Lys Leu Leu Phe Ala Ile Glu Glu Thr
        835                 840                 845
```

```
Glu Gly Phe Gly Gln Glu
    850
```

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: unknown
        (D) TOPOLOGY: unknown (ii) MOLECULE TYPE: Other (xi) SEQUENCE DESCRIPTION: SEQ ID NO:5:

ATGGGTAGCC TCACCATGAA A                                      21

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: unknown
        (D) TOPOLOGY: unknown (ii) MOLECULE TYPE: Other (xi) SEQUENCE DESCRIPTION: SEQ ID NO:6:

TTACTCTTGT CCAAATCCTT C                                      21

(2) INFORMATION FOR SEQ ID NO:7:

(i) SEQUENCE CHARACTERISTICS:
        (A) LENGTH: 156 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:7:

```
Met Gln Ile Phe Val Lys Thr Leu Thr Gly Lys Thr Ile Thr Leu Glu
  1                 5                  10                  15
```

```
Val Glu Pro Ser Asp Thr Ile Glu Asn Val Lys Ala Lys Ile Gln Asp
            20                  25                  30
```

```
Lys Glu Gly Ile Pro Pro Asp Gln Gln Arg Leu Ile Phe Ala Gly Lys
        35                  40                  45
```

```
Gln Leu Glu Asp Gly Arg Thr Leu Ser Asp Tyr Asn Ile Gln Lys Glu
 50                  55                  60
```

```
Ser Thr Leu His Leu Val Leu Arg Leu Arg Gly Gly Ala Lys Lys Arg
 65                  70                  75                  80
```

```
Lys Lys Lys Ser Tyr Thr Thr Pro Lys Lys Asn Lys His Lys Arg Lys
                85                  90                  95
```

```
Lys Val Lys Leu Ala Val Leu Lys Tyr Tyr Lys Val Asp Glu Asn Gly
            100                 105                 110
```

```
Lys Ile Ser Arg Leu Arg Arg Glu Cys Pro Ser Asp Glu Cys Gly Ala
        115                 120                 125
```

```
Gly Val Phe Met Ala Ser His Phe Asp Arg His Tyr Cys Gly Lys Cys
    130                 135                 140
```

```
Cys Leu Thr Tyr Cys Phe Asn Lys Pro Glu Asp Lys
```

(2) INFORMATION FOR SEQ ID NO:8:

(i) SEQUENCE CHARACTERISTICS:
        (A) LENGTH: 76 amino acids
        (B) TYPE: amino acid
        (C) STRANDEDNESS: unknown
        (D) TOPOLOGY: unknown (ii) MOLECULE TYPE: peptide (xi) SEQUENCE DESCRIPTION: SEQ ID NO:8:

```
Met Gln Ile Phe Val Lys Thr Leu Thr Gly Lys Thr Ile Thr Leu Glu
 1               5                  10                  15

Val Glu Pro Ser Asp Thr Ile Glu Asn Val Lys Ala Lys Ile Gln Asp
             20                  25                  30

Lys Glu Gly Ile Pro Pro Asp Gln Gln Arg Leu Ile Phe Ala Gly Lys
         35                  40                  45

Gln Leu Glu Asp Gly Arg Thr Leu Ser Asp Tyr Asn Ile Gln Lys Glu
     50                  55                  60

Ser Thr Leu His Leu Val Leu Arg Leu Arg Gly Gly
 65                  70                  75
```

(2) INFORMATION FOR SEQ ID NO:9:

(i) SEQUENCE CHARACTERISTICS:
        (A) LENGTH: 471 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO:9:

```
ATGCAGATTT TCGTGAAAAC CCTTACGGGG AAGACCATCA CCCTCGAGGT TGAACCCTCG      60
GATACGATAG AAAATGTAAA GGCCAAGATC CAGGATAAGG AAGGAATTCC TCCTGATCAG     120
CAGAGACTGA TCTTTGCTGG CAAGCAGCTG AAGATGGAC GTACTTTGTC TGACTACAAT      180
ATTCAAAAGG AGTCTACTCT TCATCTTGTG TTGAGACTTC GTGGTGGTGC TAAGAAAAGG     240
AAGAAGAAGT CTTACACCAC TCCCAAGAAG AATAAGCACA AGAGAAAGAA GGTTAAGCTG     300
GCTGTCCTGA ATATTATAA GGTGGATGAG AATGGCAAAA TTAGTCGCCT TCGTCGAGAG      360
TGCCCTTCTG ATGAATGTGG TGCTGGGGTG TTTATGGCAA GTCACTTTGA CAGACATTAT     420
TGTGGCAAAT GTTGTCTGAC TTACTGTTTC AACAAACCAG AAGACAAGTA A              471
```

(2) INFORMATION FOR SEQ ID NO:10:

(i) SEQUENCE CHARACTERISTICS:
        (A) LENGTH: 3177 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO:10:

```
ATGTCCAGCT CGCCGCTGTC CAAGAAACGT CGCGTGTCCG GGCCTGATCC AAAGCCGGGT      60
TCTAACTGCT CCCCTGCCCA GTCCGTGTTG TCCGAAGTGC CCTCGGTGCC AACCAACGGA     120
ATGGCCAAGA ACGGCAGTGA AGCAGACATA GACGAGGGCC TTTACTCCCG GCAGCTGTAT     180
GTGTTGGGCC ATGAGGCAAT GAAGCGGCTC CAGACATCCA GTGTCCTGGT ATCAGGCCTG     240
```

-continued

| | |
|---|---|
| CGGGGCCTGG GCGTGGAGAT CGCTAAGAAC ATCATCCTTG GTGGGGTCAA GGCTGTTACC | 300 |
| CTACATGACC AGGGCACTGC CCAGTGGGCT GATCTTTCCT CCCAGTTCTA CCTGCGGGAG | 360 |
| GAGGACATCG GTAAAAACCG GGCCGAGGTA TCACAGCCCC GCCTCGCTGA GCTCAACAGC | 420 |
| TATGTGCCTG TCACTGCCTA CACTGGACCC CTCGTTGAGG ACTTCCTTAG TGGTTTCCAG | 480 |
| GTGGTGGTGC TCACCAACAC CCCCCTGGAG GACCAGCTGC GAGTGGGTGA GTTCTGTCAC | 540 |
| AACCGTGGCA TCAAGCTGGT GGTGGCAGGC ACGCGGGGCC TGTTTGGGCA GCTCTTCTGT | 600 |
| GACTTTGGAG AGGAAATGAT CCTCACAGAT TCCAATGGGG AGCAGCCACT CAGTGCTATG | 660 |
| GTTTCTATGG TTACCAAGGA CAACCCCGGT GTGGTTACCT GCCTGGATGA GGCCCGACAC | 720 |
| GGGTTTGAGA GCGGGACTT TGTCTCCTTT TCAGAAGTAC AGGGCATGGT TGAACTCAAC | 780 |
| GGAAATCAGC CCATGGAGAT CAAAGTCCTG GGTCCTTATA CCTTTAGCAT CTGTGACACC | 840 |
| TCCAACTTCT CCGACTACAT CCGTGGAGGC ATCGTCAGTC AGGTCAAAGT ACCTAAGAAG | 900 |
| ATTAGCTTTA AATCCTTGGT GGCCTCACTG GCAGAACCTG ACTTTGTGGT GACGGACTTC | 960 |
| GCCAAGTTTT CTCGCCCTGC CCAGCTGCAC ATTGGCTTCC AGGCCCTGCA CCAGTTCTGT | 1020 |
| GCTCAGCATG GCCGGCCACC TCGGCCCCGC AATGAGGAGG ATGCAGCAGA ACTGGTAGCC | 1080 |
| TTAGCACAGG CTGTGAATGC TCGAGCCCTG CCAGCAGTGC AGCAAAATAA CCTGGACGAG | 1140 |
| GACCTCATCC GGAAGCTGGC ATATGTGGCT GCTGGGGATC TGGCACCCAT AAACGCCTTC | 1200 |
| ATTGGGGGCC TGGCTGCCCA GGAAGTCATG AAGGCCTGCT CCGGGAAGTT CATGCCCATC | 1260 |
| ATGCAGTGGC TATACTTTGA TGCCCTTGAG TGTCTCCCTC AGGACAAAGA GGTCCTCACA | 1320 |
| GAGGACAAGT GCCTCCAGCG CCAGAACCGT TATGACGGGC AAGTGGCTGT GTTTGGCTCA | 1380 |
| GACCTGCAAG AGAAGCTGGG CAAGCAGAAG TATTTCCTGG TGGGTGCGGG GGCCATTGGC | 1440 |
| TGTGAGCTGC TCAAGAACTT TGCCATGATT GGGCTGGGCT GCGGGGAGGG TGGAGAAATC | 1500 |
| ATCGTTACAG ACATGGACAC CATTGAGAAG TCAAATCTGA ATCGACAGTT TCTTTTCCGG | 1560 |
| CCCTGGGATG TCACGAAGTT AAAGTCTGAC ACGGCTGCTG CAGCTGTGCG CCAAATGAAT | 1620 |
| CCACATATCC GGGTGACAAG CCACCAGAAC CGTGTGGGTC CTGACACGGA GCGCATCTAT | 1680 |
| GATGACGATT TTTTCCAAAA CCTAGATGGC GTGGCCAATG CCCTGGACAA CGTGGATGCC | 1740 |
| CGCATGTACA TGGACCGCCG CTGTGTCTAC TACCGGAAGC CACTGCTGGA GTCAGGCACA | 1800 |
| CTGGGCACCA AAGGCAATGT GCAGGTGGTG ATCCCCTTCC TGACAGAGTC GTACAGTTCC | 1860 |
| AGCCAGGACC CACCTGAGAA GTCCATCCCC ATCTGTACCC TGAAGAACTT CCCTAATGCC | 1920 |
| ATCGAGCACA CCCTGCAGTG GGCTCGGGAT GAGTTTGAAG GCCTCTTCAA GCAGCCAGCA | 1980 |
| GAAAATGTCA ACCAGTACCT CACAGACCCC AAGTTTGTGG AGCGAACACT GCGGCTGGCA | 2040 |
| GGCACTCAGC CCTTGGAGGT GCTGGAGGCT GTGCAGCGCA GCCTGGTGCT GCAGCGACCA | 2100 |
| CAGACCTGGG CTGACTGCGT GACCTGGGCC TGCCACCACT GGCACACCCA GTACTCGAAC | 2160 |
| AACATCCGGC AGCTGCTGCA CAACTTCCCT CCTGACCAGC TCACAAGCTC AGGAGCGCCG | 2220 |
| TTCTGGTCTG GGCCCAAACG CTGTCCACAC CCGCTCACCT TTGATGTCAA CAATCCCCTG | 2280 |
| CATCTGGACT ATGTGATGGC TGCTGCCAAC CTGTTTGCCC AGACCTACGG GCTGACAGGC | 2340 |
| TCTCAGGACC GAGCTGCTGT GGCCACATTC CTGCAGTCTG TGCAGGTCCC CGAATTCACC | 2400 |
| CCCAAGTCTG GCGTCAAGAT CCATGTTTCT GACCAGGAGC TGCAGAGCGC CAATGCCTCT | 2460 |
| GTTGATGACA GTCGTCTAGA GGAGCTCAAA GCCACTCTGC CCAGCCCAGA CAAGCTCCCT | 2520 |
| GGATTCAAGA TGTACCCCAT TGACTTTGAG AAGGATGATG ACAGCAACTT TCATATGGAT | 2580 |
| TTCATCGTGG CTGCATCCAA CCTCCGGGCA GAAAACTATG ACATTCCTTC TGCAGACCGG | 2640 |

-continued

```
CACAAGAGCA AGCTGATTGC AGGGAAGATC ATCCCAGCCA TTGCCACGAC CACAGCAGCC     2700

GTGGTTGGCC TTGTGTGTCT GGAGCTGTAC AAGGTTGTGC AGGGGCACCG ACAGCTTGAC     2760

TCCTACAAGA ATGGTTTCCT CAACTTGGCC CTGCCTTTCT TTGGTTTCTC TGAACCCCTT     2820

GCCGCACCAC GTCACCAGTA CTATAACCAA GAGTGGACAT TGTGGGATCG CTTTGAGGTA     2880

CAAGGGCTGC AGCCTAATGG TGAGGAGATG ACCCTCAAAC AGTTCCTCGA CTATTTTAAG     2940

ACAGAGCACA AATTAGAGAT CACCATGCTG TCCCAGGGCG TGTCCATGCT CTATTCCTTC     3000

TTCATGCCAG CTGCCAAGCT CAAGGAACGG TTGGATCAGC CGATGACAGA GATTGTGAGC     3060

CGTGTGTCGA AGCGAAAGCT GGGCCGCCAC GTGCGGGCGC TGGTGCTTGA GCTGTGCTGT     3120

AACGACGAGA GCGGCGAGGA TGTCGAGGTT CCCTATGTCC GATACACCAT CCGCTGA       3177

(2) INFORMATION FOR SEQ ID NO:11:

(i) SEQUENCE CHARACTERISTICS:
        (A) LENGTH: 444 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO:11:

ATGGCGCTGA AACGGATTAA TAAGGAACTT AGTGATTTGG CCCGTGACCC TCCAGCACAA       60

TGTTCTGCAG GTCCAGTTGG AGATGACATG TTTCATTGGC AAGCCACAAT TATGGGACCT      120

AATGACAGCC CATATCAAGG TGGTGTATTC TTTTTGACAA TTCATTTTCC TACAGACTAC      180

CCCTTCAAAC CACCTAAGGT TGCATTTACA ACAAGAATTT ATCATCCAAA TATTAACAGT      240

AATGGCAGCA TTTGTCTTGA TATTCTAAGA TCACAGTGGT CTCCTGCTTT AACTATTTCT      300

AAAGTTCTTT TATCCATTTG TTCACTGCTA TGTGATCCAA ACCCAGATGA CCCCCTAGTG      360

CCAGAGATTG CACGGATCTA TAAAACAGAC AGAGACAAGT ACAACAGAAT ATCTCGGGAA      420

TGGACTCAGA AGTATGCCAT GTGA                                             444
```